United States Patent
Scifert et al.

(10) Patent No.: US 8,469,964 B2
(45) Date of Patent: Jun. 25, 2013

(54) BONE CUTTING TEMPLATE AND METHOD OF TREATING BONE FRACTURES

(75) Inventors: Jeffrey L. Scifert, Arlington, TN (US); Scott D. Boden, Atlanta, GA (US); James S. Marotta, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 1340 days.

(21) Appl. No.: 11/431,693

(22) Filed: May 10, 2006

(65) Prior Publication Data
US 2007/0265632 A1    Nov. 15, 2007

(51) Int. Cl.
*A61B 17/56* (2006.01)
*A61B 17/90* (2006.01)
*A61B 17/15* (2006.01)

(52) U.S. Cl.
USPC .................. 606/102; 606/86 R; 33/512

(58) Field of Classification Search
USPC ... 606/53, 86 R, 87, 96, 97, 102, 82; D10/71; 33/483–484, 511, 512
See application file for complete search history.

(56) References Cited

U.S. PATENT DOCUMENTS

| | | | | | |
|---|---|---|---|---|---|
| 442,020 | A | * | 12/1890 | Darling | 33/483 |
| 443,652 | A | * | 12/1890 | Jewell et al. | 33/483 |
| 501,494 | A | * | 7/1893 | Wilson | 432/99 |
| 1,870,655 | A | * | 8/1932 | Schur | 235/69 |
| 2,382,758 | A | * | 8/1945 | Weeks et al. | 33/484 |
| 2,543,476 | A | * | 2/1951 | Southern | 33/484 |
| 2,616,181 | A | * | 11/1952 | Van Doorne | 33/484 |
| 2,642,674 | A | * | 6/1953 | Schell, Jr. | 33/527 |
| D271,821 | S | * | 12/1983 | Kelson | D3/18 |
| D281,301 | S | * | 11/1985 | Spolar | D10/46.2 |
| 4,930,227 | A | * | 6/1990 | Ketchpel | 33/755 |
| 5,251,642 | A | * | 10/1993 | Handlos | 600/587 |
| 5,413,579 | A | * | 5/1995 | Tom Du Toit | 606/87 |
| 5,470,335 | A | * | 11/1995 | Du Toit | 606/329 |
| 5,697,933 | A | * | 12/1997 | Gundlapalli et al. | 606/96 |
| D399,442 | S | * | 10/1998 | Bedol | D10/71 |
| 5,899,939 | A | | 5/1999 | Boyce et al. | |
| D448,687 | S | * | 10/2001 | Landwerlen | D10/71 |
| 6,579,857 | B1 | | 6/2003 | Lind et al. | |
| D478,519 | S | * | 8/2003 | Black | D10/71 |
| D486,747 | S | * | 2/2004 | Shapiro | D10/71 |
| D493,735 | S | * | 8/2004 | Shapiro | D10/71 |
| 6,843,279 | B1 | * | 1/2005 | Ungemah | 138/149 |
| D627,055 | S | * | 11/2010 | Bain | D24/105 |
| D637,925 | S | * | 5/2011 | Groover et al. | D10/71 |
| 2001/0018614 | A1 | | 8/2001 | Bianchi | |
| 2003/0158558 | A1 | * | 8/2003 | Horn | 606/87 |
| 2003/0181920 | A1 | | 9/2003 | Hawkins et al. | |
| 2003/0191475 | A1 | * | 10/2003 | McGuire | 606/102 |
| 2004/0002758 | A1 | * | 1/2004 | Landry et al. | 623/17.11 |
| 2004/0035012 | A1 | * | 2/2004 | Moehnke et al. | 33/494 |
| 2006/0247791 | A1 | | 11/2006 | McKay et al. | |

\* cited by examiner

*Primary Examiner* — Michael T Schaper
(74) *Attorney, Agent, or Firm* — Sorell Lenna & Schmidt LLP

(57) ABSTRACT

A bone cutting template is disclosed and can include a body. A plurality of grooves can be formed along the body and each groove can correspond to an incremental length of the body. The bone cutting template can include a plurality of length stamps along the body. Each of the plurality of length stamps can be adjacent to a corresponding groove.

15 Claims, 16 Drawing Sheets

BONE CUTTING TEMPLATE AND METHOD OF TREATING BONE FRACTURES

FIELD OF THE DISCLOSURE

The present disclosure relates generally to orthopedics and orthopedic surgery. More specifically, the present disclosure relates to devices used to deliver drugs.

BACKGROUND

An adult human skeleton includes two hundred and six bones. During a lifetime a human may fracture one or more of these bones. Some fractures may be treated using a casting process. Certain other fractures of long bones may be treated using an intramedullary rod. For example, fractures of the ulnae, radii, humeri, femora, tibiae, and fibulae can be treated using an intramedullary rod. In such cases, the intramedullary rod can be permanently installed within these bones and the bone can be allowed to heal around the intramedullary rod.

Sometimes, these fractures can also result in a loss of bone, e.g., a bone gap, and it may be necessary to fill the bone gap with something to promote new bone growth. It can be advantageous to deliver a therapeutic agent to an area of a bone gap in addition to installing an intramedullary rod.

DETAILED DESCRIPTION OF THE DRAWINGS

A bone cutting template is disclosed and can include a body. A plurality of grooves can be formed along the body and each groove can correspond to an incremental length of the body. The bone cutting template can include a plurality of length stamps along the body. Each of the plurality of length stamps can be adjacent to a corresponding groove.

In another embodiment, a method of treating a bone fracture is disclosed and can include retrieving a bone cutting template and trimming a perimeter of a bone void within a bone around the bone cutting template.

In yet another embodiment, a kit for field use is disclosed and can include a set of bone cutting templates. Each of the set of bone cutting templates can include a plurality of grooves formed along the body and each groove can correspond to an incremental length of the body. Also, each of the set of bone cutting templates can include a plurality of length stamps along the body and each of the plurality of length stamps can be adjacent to a corresponding groove. The kit further includes a bone cutting template handle configured to removably engage each of the bone cutting templates.

In still another embodiment, a kit for field use is disclosed and can include a set of therapeutic agent carriers. Each of the set of therapeutic agent carriers can include a body shaped to approximate a portion of a bone and a plurality of grooves formed along the body. Each groove can correspond to an incremental length of the body. Each of the set of therapeutic agent carriers can also include a plurality of dosage stamps along the body and each of the plurality of dosage stamps can indicate a dose of therapeutic agent to load the body between an end of the body and a groove. The kit can also include a set of bone cutting templates and each of the set of bone cutting templates can include a plurality of grooves formed along the body. Each groove corresponds to an incremental length of the body. Each of the set of bone cutting templates can also include a plurality of length stamps along the body and each of the plurality of length stamps can be adjacent to a corresponding groove.

Description of Relevant Anatomy

Figure 1:
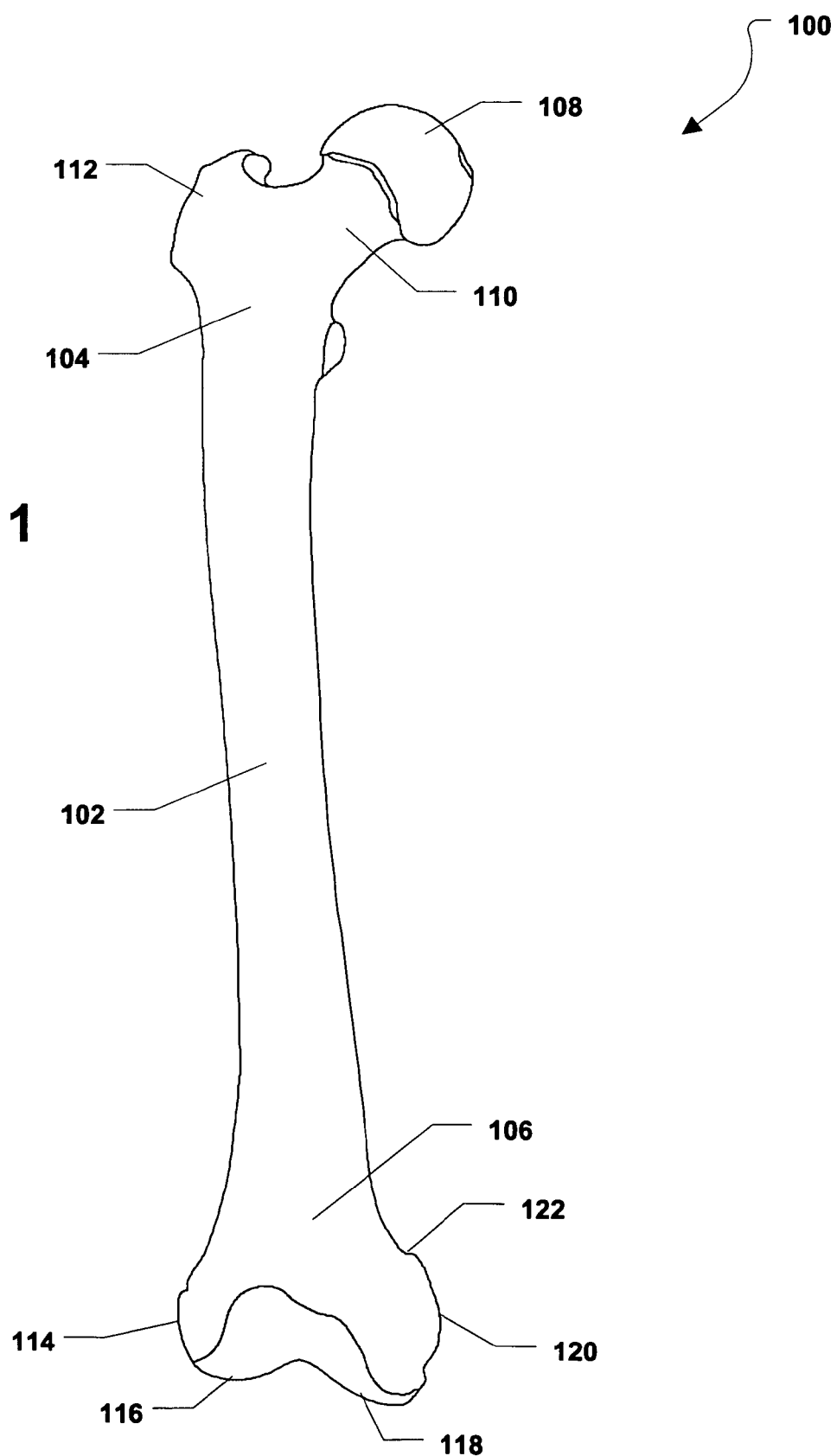
FIG. 1 is a plan view of a femur.

Referring to FIG. 1, a femur is shown and is generally designated 100. As shown, the femur 100 includes a femoral body 102 that can define a proximal end 104 and a distal end 106. Further, the femur 100 can include a femoral head 108 that extends from the proximal end 104 of the femoral body 102. Further, a neck 110 can be established between the femoral head 108 and the femoral body 102. In a particular embodiment, the femoral head 108 can fit into a hip socket, a.k.a., an acetabulum (not shown).

As further illustrated in FIG. 1, the proximal end 104 of the femoral body 102 can include a greater trochanter 112 adjacent to the neck of the proximal end 104. Additionally, the distal end 106 of the femoral body 102 can include a lateral epicondyle 114, a lateral condyle 116, a medial condyle 118, and a medial epicondyle 120. In a particular embodiment, the lateral condyle 116 and the medial condyle 118 can articulate with a patella (not shown). FIG. 1 also indicates that the femur 100 can include an adductor tubercle 122.

Description of a Set of Therapeutic Agent Carriers

Figure 2:
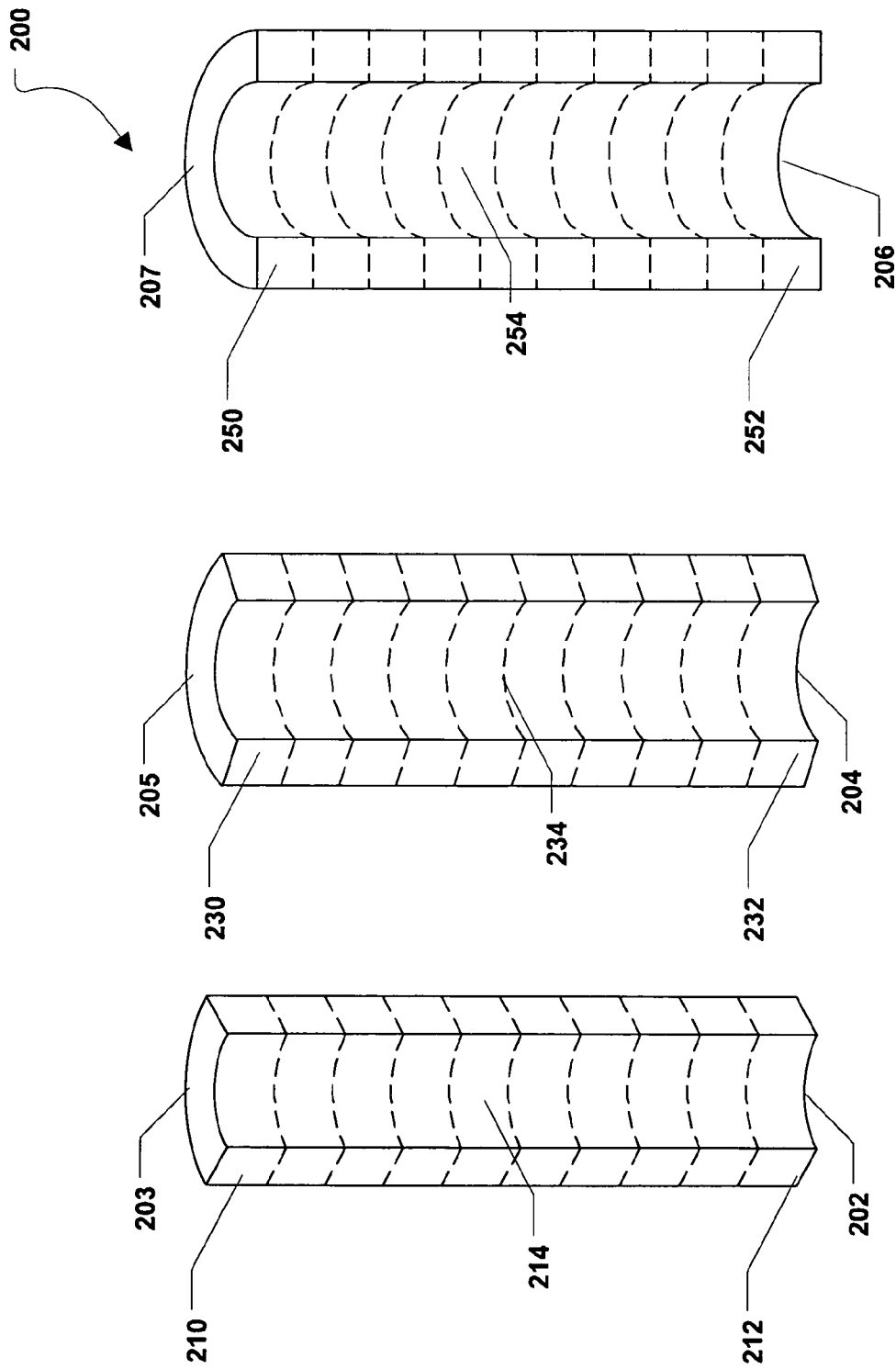
FIG. 2 is a front view of a set of therapeutic agent carriers.
Figure 3:
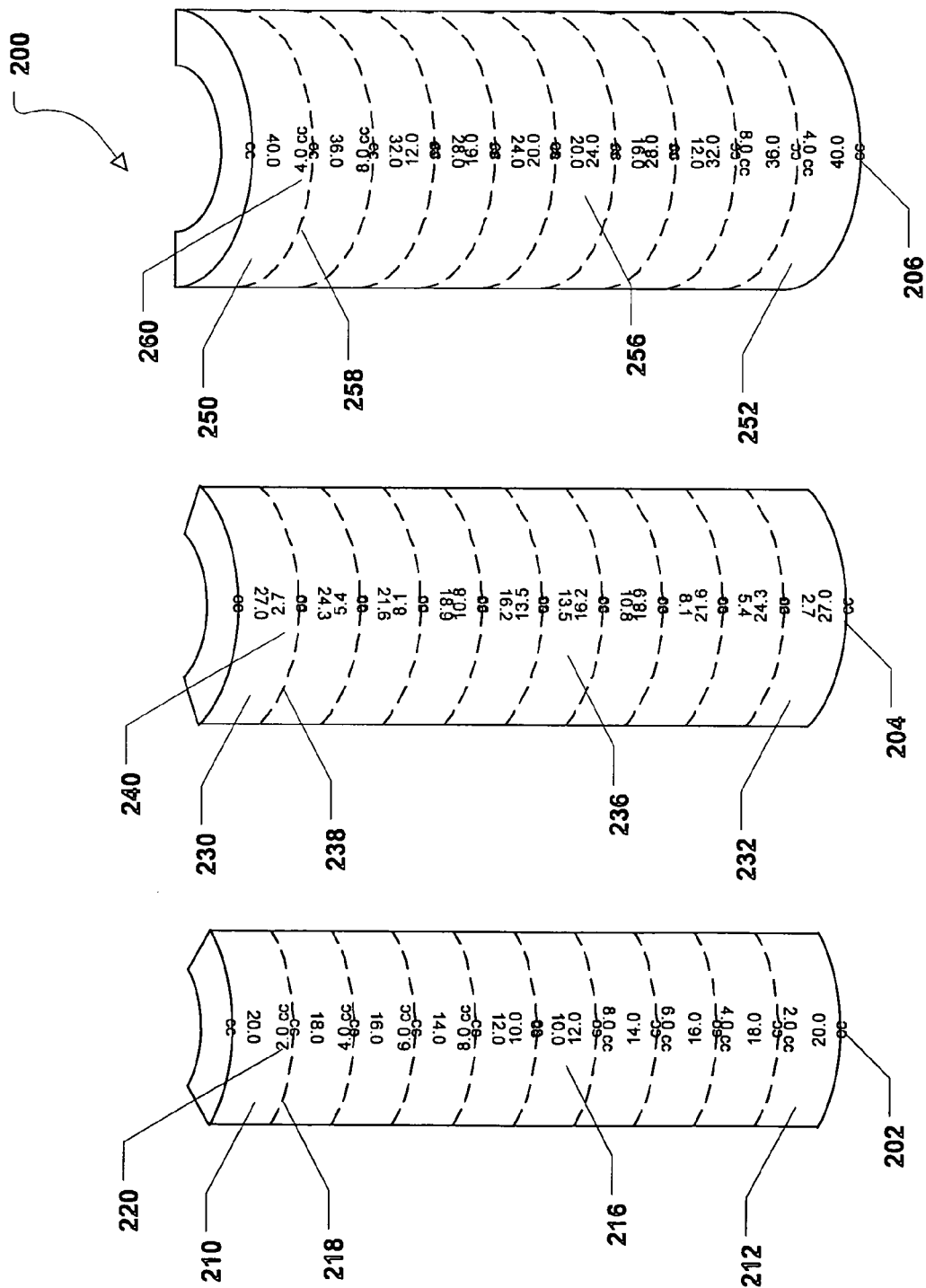
FIG. 3 is a rear view of the set of therapeutic agent carriers.
Figure 4:
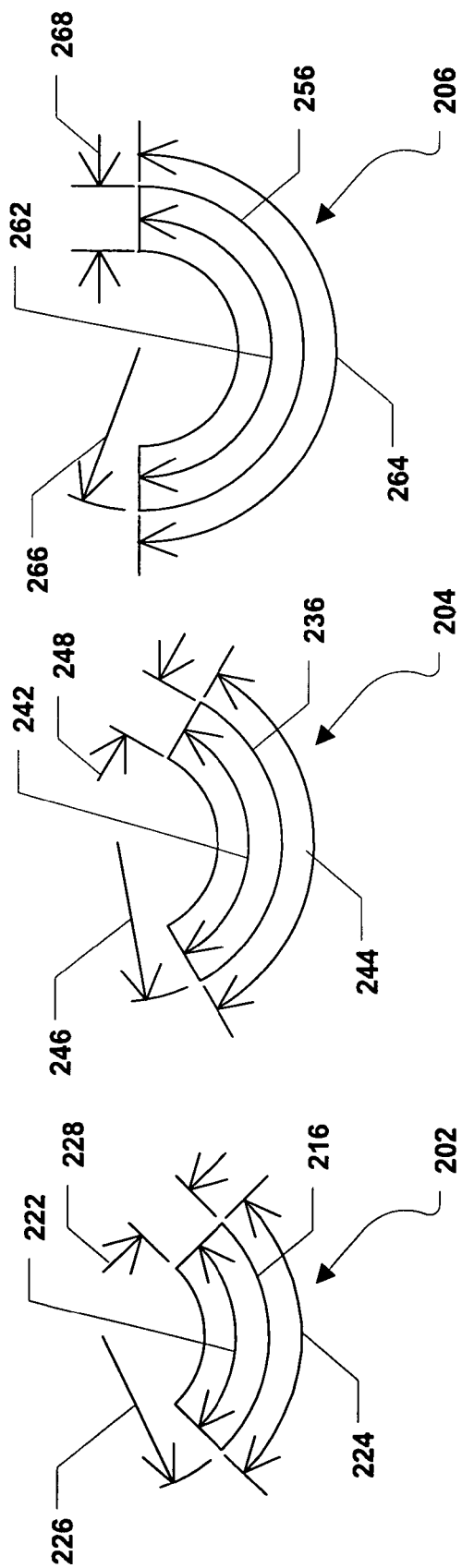
FIG. 4 is an end view of the set of therapeutic agent carriers.

Referring to FIG. 2 through FIG. 4, a set of therapeutic agent carriers is shown and is generally designated 200. As shown, the set of therapeutic agent carriers 200 can include a first therapeutic agent carrier 202, a second therapeutic agent carrier 204, and a third therapeutic agent carrier 206.

In a particular embodiment, the first therapeutic agent carrier 202 can include a body 203 having a proximal end 210 and a distal end 212. The body 203 of first therapeutic agent carrier 202 can also include an interior surface 214 and an exterior surface 216. In a particular embodiment, the body 203 of the first therapeutic agent carrier 202 can be made from a ceramic material, a collagen-ceramic material, a degradable polymer, or a combination thereof.

As illustrated in FIG. 3, the exterior surface 216 of the first therapeutic agent carrier 202 can include a plurality of incremental grooves 218 from the proximal end 210 of the first therapeutic agent carrier 202 to the distal end 212 of the therapeutic agent carrier 202. In a particular embodiment, the incremental grooves 218 can indicate incremental lengths along the first therapeutic agent carrier 202. For example, if the increment is one-half inch, a user may know that by cutting the first therapeutic agent carrier 202 along the second incremental groove 218, the first therapeutic agent carrier 202 will be approximately one inch long. Further, each incremental groove 218 can serve as a guide for a cutting device, e.g., a saw, a knife, a scalpel, scissors, or other similar device.

FIG. 3 further indicates that the therapeutic agent carrier 202 can include a dosage stamp 220 adjacent to each incremental groove 218. In a particular embodiment, each dosage stamp 220 can indicate an amount of therapeutic agent that can be used to load the first therapeutic agent carrier 202 to the associated increment groove 218. In this context, the terms "load" or "loading" means wetting, embedding, absorbing, adsorbing or otherwise introducing a therapeutic amount of the desired therapeutic agent onto or into the therapeutic agent carrier, with a "therapeutic amount" being a beneficial dosage based on clinical need. As such, if a user cuts the first therapeutic agent carrier 202 along the second incremental groove 218, as described above, the user will know that four cubic centimeters (4.0 cc) of therapeutic agent can be used to properly load the one inch long portion of the first therapeutic agent carrier 202.

The therapeutic agents can include drugs, cellular matters, biological factors, synthetic osteoinductive peptides, synthetic osteopromotive peptides, or a combination thereof. In a particular embodiment, the drugs can include antibiotics, analgesics, anti-inflammatory drugs, anti-TNF-alpha, steroids, or a combination thereof. Further, the cellular matters can include bone marrow derived stem cells, lipo derived stem cells, or a combination thereof. Also, the biological factor can include bone morphogenetic protein (BMP), cartilage-derived morphogenetic protein (CDMP), platelet derived growth factor (PDGF), insulin-like growth factor (IGF), LIM mineralization protein, fibroblast growth factor (FGF), osteoblast growth factor, growth and differentiation factor (GDF), vascular endothelial growth factor (VEGF), or a combination thereof. The synthetic osteoinductive peptide or the synthetic osteopromotive peptide can include a fragment of a thrombin molecule. Also, the GDF can include GDF-5.

In a particular embodiment, the first therapeutic agent carrier 202 can be stamped bi-directionally. In other words, the first therapeutic agent carrier 202 can be marked with a first incremental series of dosage stamps 220 that can be read when the proximal end 210 of the first therapeutic agent carrier 202 is up. Also, the first therapeutic agent carrier 202 can be marked with a second incremental series of dosage stamps 220 that can be read when the distal end 212 of the first therapeutic agent carrier 202 is up.

Accordingly, the dosage stamps 220 can indicate the proper dosage of therapeutic agent that can be used to wet the first therapeutic agent carrier 202 if the first therapeutic agent carrier 202 is cut from the proximal end 210 or the distal end 212. Further, if the first therapeutic agent carrier 202 is cut from the proximal end 210 and used to fill a bone void, or a bone gap, as described herein, the first therapeutic agent carrier 202 can also be cut from the distal end 212 and used to fill another bone gap—if the bone gap is the same length or shorter than the remaining portion of the first therapeutic agent carrier 202.

Referring now to FIG. 4, the first therapeutic agent carrier 202 has a cross-section that can follow an arc 222 having a central angle 224 that is substantially equal to ninety degrees (90°). As such, the first therapeutic agent carrier 202 has a cross-section that is equal to one-quarter of a hollow cylinder. Further, the exterior surface 216 of the first therapeutic agent carrier 202 can define a radius 226. In a particular embodiment, the radius 226 of the exterior surface 216 can be configured to approximate the outer cortex of a bone to be treated. For example, the radius 226 of the exterior surface 216 can be in a range from one centimeter (1 cm) to six centimeters (6 cm). Further, for treating radii bones, the radius 226 can be in a range from two centimeters (2 cm) to three and one-half centimeters (3.5 cm). Also, for treating femurs, the radius 226 can be in a range from two centimeters (2 cm) to four centimeters (4 cm). Also, the first therapeutic agent carrier 202 can have a thickness 228. In a particular embodiment, the thickness 228 of the first therapeutic agent carrier 202 can be in a range from one centimeter (1 cm) to six centimeters (6 cm).

In a particular embodiment, the second therapeutic agent carrier 204 can include a body 205 having a proximal end 230 and a distal end 232. The body 205 of the second therapeutic agent carrier 204 can also include an interior surface 234 and an exterior surface 236. In a particular embodiment, the body 205 of the second therapeutic agent carrier 204 can be made from a ceramic material, a collagen-ceramic material, a degradable polymer, or a combination thereof.

As illustrated in FIG. 3, the exterior surface 236 of the second therapeutic agent carrier 204 can include a plurality of incremental grooves 238 from the proximal end 230 of the second therapeutic agent carrier 204 to the distal end 232 of the therapeutic agent carrier 204. In a particular embodiment, the incremental grooves 238 can indicate incremental lengths along the second therapeutic agent carrier 204. For example, if the increment is one-half inch, a user may know that by cutting the second therapeutic agent carrier 204 along the second incremental groove 238, the second therapeutic agent carrier 204 will be approximately one inch long. Further, each incremental groove 238 can serve as a guide for a cutting device, e.g., a saw, a knife, a scalpel, scissors, or other similar device.

FIG. 3 further indicates that the second therapeutic agent carrier 204 can include a dosage stamp 240 adjacent to each incremental groove 238. In a particular embodiment, each dosage stamp 240 can indicate an amount of therapeutic agent that can be used to load the second therapeutic agent carrier 204 to the associated increment groove 238. In this context, the terms "load" or "loading" means wetting, embedding, absorbing, adsorbing, or otherwise introducing a therapeutic amount of the desired therapeutic agent onto or into the therapeutic agent carrier, with a "therapeutic amount" being a beneficial dosage based on clinical need. As such, if a user cuts the second therapeutic agent carrier 204 along the second incremental groove 238, as described above, the user will know that four cubic centimeters (4.0 cc) of therapeutic agent can be used to properly load the one inch long portion of the second therapeutic agent carrier 204.

The therapeutic agents can include drugs, cellular matters, biological factors, synthetic osteoinductive peptides, synthetic osteopromotive peptides, or a combination thereof. In a particular embodiment, the drugs can include antibiotics, analgesics, anti-inflammatory drugs, anti-TNF-alpha, steroids, or a combination thereof. Further, the cellular matters can include bone marrow derived stem cells, lipo derived stem cells, or a combination thereof. Also, the biological factor can include bone morphogenetic protein (BMP), cartilage-derived morphogenetic protein (CDMP), platelet derived growth factor (PDGF), insulin-like growth factor (IGF), LIM mineralization protein, fibroblast growth factor (FGF), osteoblast growth factor, growth and differentiation factor (GDF), vascular endothelial growth factor (VEGF), or a combination thereof. The synthetic osteoinductive peptide or the synthetic osteopromotive peptide can include a fragment of a thrombin molecule. Also, the GDF can include GDF-5.

In a particular embodiment, the second therapeutic agent carrier 204 can be stamped bi-directionally. In other words, the second therapeutic agent carrier 204 can be marked with a second incremental series of dosage stamps 240 that can be read when the proximal end 230 of the second therapeutic agent carrier 204 is up. Also, the second therapeutic agent carrier 204 can be marked with a second incremental series of dosage stamps 240 that can be read when the distal end 232 of the second therapeutic agent carrier 204 is up.

Accordingly, the dosage stamps 240 can indicate the proper dosage of therapeutic agent that can be used to wet the second therapeutic agent carrier 204 if the second therapeutic agent carrier 204 is cut from the proximal end 230 or the distal end 232. Further, if the second therapeutic agent carrier 204 is cut from the proximal end 230 and used to fill a bone gap as described herein, the second therapeutic agent carrier 204 can also be cut from the distal end 232 and used to fill another bone gap—if the bone gap is the same length or shorter than the remaining portion of the second therapeutic agent carrier 204.

Referring now to FIG. 4, the second therapeutic agent carrier 204 has a cross-section that can follow an arc 242 having a central angle 244 that is substantially equal to one hundred and twenty degrees (120°). As such, the second therapeutic agent carrier 204 has a cross-section that is equal to one-third of a hollow cylinder. Further, the exterior surface 236 of the second therapeutic agent carrier 204 can define a radius 246. In a particular embodiment, the radius 246 of the exterior surface 236 can be configured to approximate the outer cortex of a bone to be treated. For example, the radius 246 of the exterior surface 236 can be in a range from one centimeter (1 cm) to six centimeters (6 cm). Further, for treating radii bones, the radius 246 can be in a range from two centimeters (2 cm) to three and one-half centimeters (3.5 cm). Also, for treating femurs, the radius 246 can be in a range from two centimeters (2 cm) to four centimeters (4 cm). Also, the second therapeutic agent carrier 204 can have a thickness 248. In a particular embodiment, the thickness 248 of the second therapeutic agent carrier 204 can be in a range from one centimeter (1 cm) to six centimeters (6 cm).

In a particular embodiment, the third therapeutic agent carrier 206 can include a body 207 having a proximal end 250 and a distal end 252. The body 207 of the third therapeutic agent carrier 206 can also include an interior surface 254 and an exterior surface 256. In a particular embodiment, the body 207 of the third therapeutic agent carrier 206 can be made from a ceramic material, a collagen-ceramic material, a degradable polymer, or a combination thereof.

As illustrated in FIG. 3,. the exterior surface 256 of the third therapeutic agent carrier 206 can include a plurality of incremental grooves 258 from the proximal end 250 of the third therapeutic agent carrier 206 to the distal end 252 of the therapeutic agent carrier 206. In a particular embodiment, the incremental grooves 258 can indicate incremental lengths along the third therapeutic agent carrier 206. For example, if the increment is one-half inch, a user may know that by cutting the third therapeutic agent carrier 206 along the second incremental groove 258, the third therapeutic agent carrier 206 will be approximately one inch long. Further, each incremental groove 258 can serve as a guide for a cutting device, e.g., a saw, a knife, a scalpel, scissors, or other similar device.

FIG. 3 further indicates that the therapeutic agent carrier 206 can include a dosage stamp 260 adjacent to each incremental groove 258. In a particular embodiment, each dosage stamp 260 can indicate an amount of therapeutic agent that can be used to load the third therapeutic agent carrier 206 to the associated increment groove 258. In this context, the terms "load" or "loading" means wetting, embedding, absorbing, adsorbing, or otherwise introducing a therapeutic amount of the desired therapeutic agent onto or into the therapeutic agent carrier, with a "therapeutic amount" being a beneficial dosage based on clinical need. As such, if a user cuts the third therapeutic agent carrier 206 along the second incremental groove 258, as described above, the user will know that four cubic centimeters (4.0 cc) of therapeutic agent can be used to properly load the one inch long portion of the third therapeutic agent carrier 206.

The therapeutic agents can include drugs, cellular matters, biological factors, synthetic osteoinductive peptides, synthetic osteopromotive peptides, or a combination thereof. In a particular embodiment, the drugs can include antibiotics, analgesics, anti-inflammatory drugs, anti-TNF-alpha, steroids, or a combination thereof. Further, the cellular matters can include bone marrow derived stem cells, lipo derived stem cells, or a combination thereof. Also, the biological factor can include bone morphogenetic protein (BMP), cartilage-derived morphogenetic protein (CDMP), platelet derived growth factor (PDGF), insulin-like growth factor (IGF), LIM mineralization protein, fibroblast growth factor (FGF), osteoblast growth factor, growth and differentiation factor (GDF), vascular endothelial growth factor (VEGF), or a combination thereof. The synthetic osteoinductive peptide or the synthetic osteopromotive peptide can include a fragment of a thrombin molecule. Also, the GDF can include GDF-5.

In a particular embodiment, the third therapeutic agent carrier 206 can be stamped bi-directionally. In other words, the third therapeutic agent carrier 206 can be marked with a third incremental series of dosage stamps 260 that can be read when the proximal end 250 of the third therapeutic agent carrier 206 is up. Also, the third therapeutic agent carrier 206 can be marked with a second incremental series of dosage stamps 260 that can be read when the distal end 252 of the third therapeutic agent carrier 206 is up.

Accordingly, the dosage stamps 260 can indicate the proper dosage of therapeutic agent that can be used to wet the third therapeutic agent carrier 206 if the third therapeutic agent carrier 206 is cut from the proximal end 250 or the distal end 252. Further, if the third therapeutic agent carrier 206 is cut from the proximal end 250 and used to fill a bone gap as described herein, the third therapeutic agent carrier 206 can also be cut from the distal end 252 and used to fill another bone gap - if the bone gap is the same length or shorter than the remaining portion of the third therapeutic agent carrier 206.

Referring now to FIG. 4, the third therapeutic agent carrier 206 has a cross-section that can follow an arc 262 having a central angle 264 that is substantially equal to one hundred and eighty degrees (180°). As such, the third therapeutic agent carrier 206 has a cross-section that is equal to one-half of a hollow cylinder, i.e., the third therapeutic agent carrier 206 has a cross-section that is equal to a hollow semi-cylinder. Further, the exterior surface 256 of the third therapeutic agent carrier 206 can define a radius 266. In a particular embodiment, the radius 266 of the exterior surface 256 can be configured to approximate the outer cortex of a bone to be treated. For example, the radius 266 of the exterior surface 256 can be in a range from one centimeter (1 cm) to six centimeters (6 cm). Further, for treating radii bones, the radius 266 can be in a range from two centimeters (2 cm) to three and one-half centimeters (3.5 cm). Also, for treating femurs, the radius 266 can be in a range from two centimeters (2 cm) to four centimeters (4 cm). Also, the third therapeutic agent carrier 206 can have a thickness 268. In a particular embodiment, the thickness 268 of the third therapeutic agent carrier 206 can be in a range from one centimeter (1 cm) to six centimeters (6 cm).

Description of a Therapeutic Agent Carrier Installed within a Bone Defect

Figure 5:
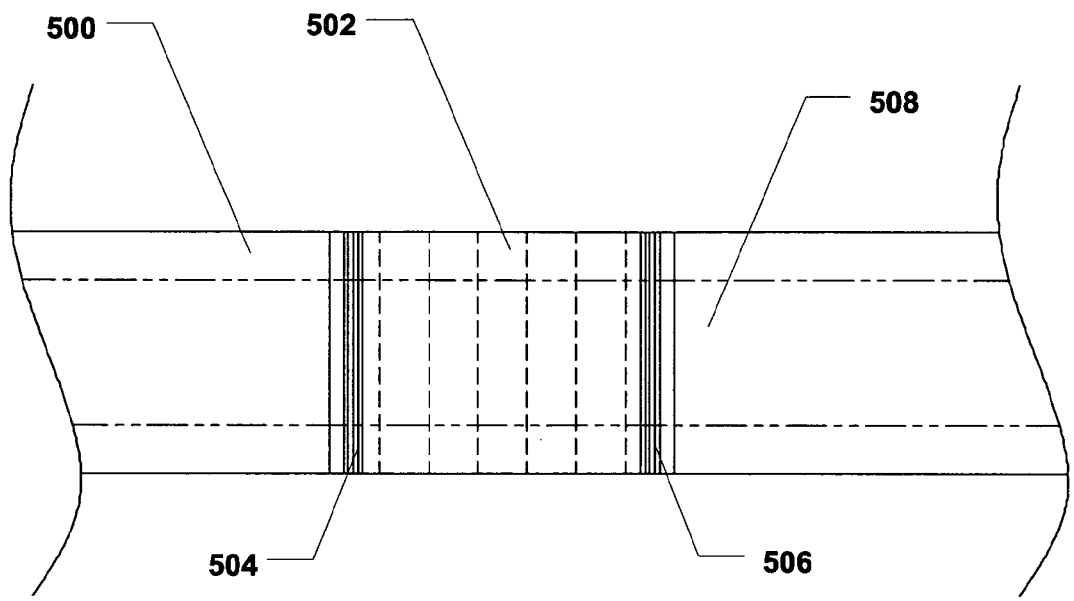
FIG. 5 is a plan view of a therapeutic agent carrier around a bone.

Referring now to FIG. 5, a bone is shown and is generally designated 500. The bone 500 can include a defect (not shown) into or over which a therapeutic agent carrier 502 can be inserted, disposed, or otherwise cover. In a particular embodiment the bone defect can be a gap in which bone has been removed or lost due to injury. Further, in a particular embodiment, the therapeutic agent carrier 502 can be a therapeutic agent carrier according to one or more of the embodiments described herein.

As depicted, the therapeutic agent carrier 502 can be installed substantially within the bone defect to replace the missing bone. Further, the therapeutic agent carrier 502 can be held in place by one or more sutures 504, 506 that can be wound around, or otherwise affixed to, the therapeutic agent carrier 502 and the bone 500. Also, in a particular embodiment, the therapeutic agent carrier 502 can be used to treat a fracture in conjunction with an intramedullary device 508, e.g., an intramedullary rod, an intramedullary nail, or a combination thereof.

Description of a First Method of Treating a Bone Fracture

Figure 6:
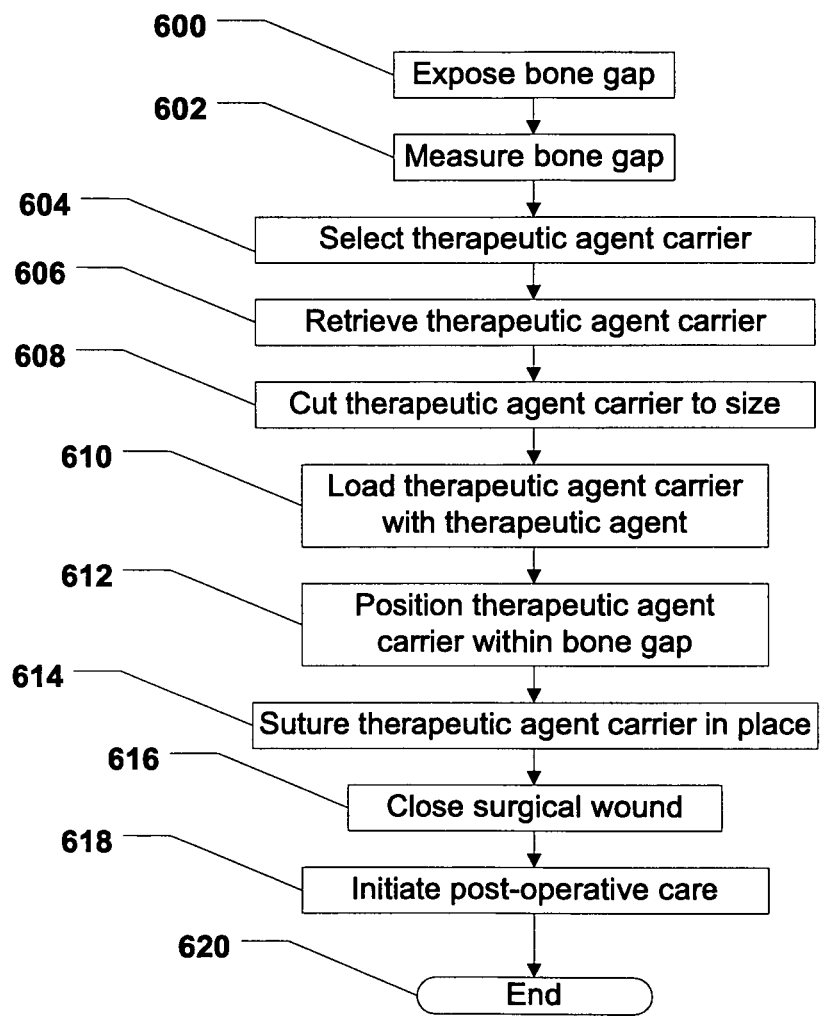
FIG. 6 is a flow chart of a first method of treating a bone fracture.

Referring to FIG. 6, a method of treating a bone fracture is shown and commences at block 600. At block 600, a bone gap due to a fracture in the bone can be exposed. At block 602, the bone gap can be measured. Further, at block 604, a therapeutic agent carrier can be selected from a set of therapeutic agent carriers. The therapeutic agent carrier can be selected based on the type of bone having the fracture, the size of the bone, the size of the bone gap, or a combination thereof.

Proceeding to block 606, the selected therapeutic agent carrier can be retrieved from the set of therapeutic agent carriers. At block 608, the therapeutic agent carrier can be cut to size. For example, the therapeutic agent carrier can be sized based on the size of the bone gap measured above. Further, the therapeutic agent carrier can be trimmed to fit the shape of the bone gap. Moving to block 610, the therapeutic agent carrier can be loaded with a therapeutic agent. At block 612, the therapeutic agent carrier can be positioned within the bone gap. Thereafter, at block 614, the therapeutic agent carrier can be sutured in place.

Continuing to block 616, the surgical wound associated with exposing the bone gap can be closed. The surgical wound can be closed by simply allowing the patient's skin to close due to the elasticity of the skin. Alternatively, the surgical wound can be closed using sutures, surgical staples, or any other suitable surgical technique well known in the art. At block 618, post-operative care can be initiated. The method then ends at state 620.

In a particular embodiment, as indicated in FIG. 6, the therapeutic agent carrier can be wetted prior to placement within the bone gap. However, in an alternative embodiment, the therapeutic agent carrier can be wetted after placement within the bone gap.

Description of a Second Method of Treating a Bone Fracture

Figure 7:
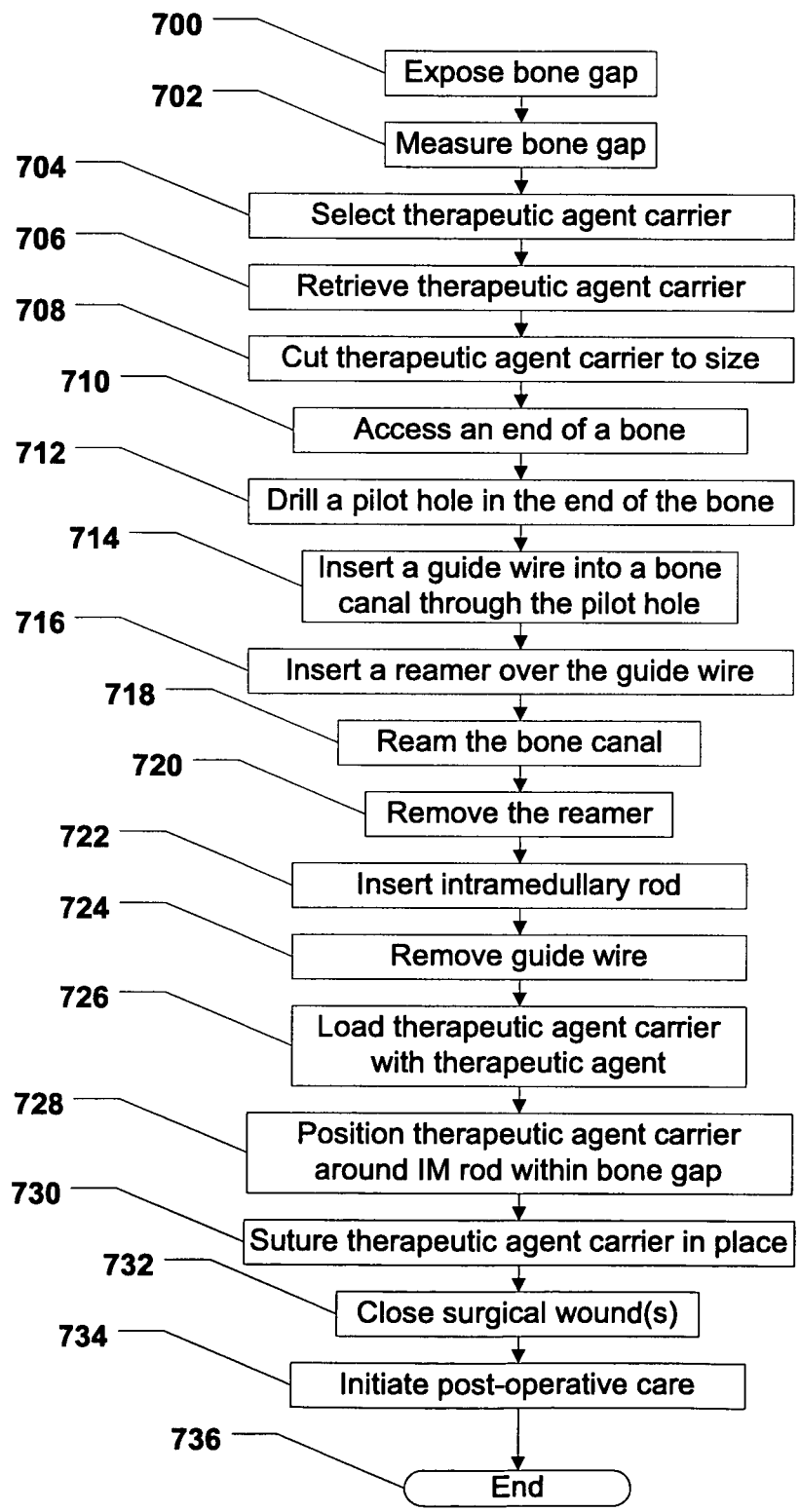
FIG. 7 is a flow chart of a second method of treating a bone fracture.

Referring to FIG. 7, a second method of treating a bone fracture is shown and commences at block 700. At block 700, a bone gap due to a fracture in the bone can be exposed. At block 702, the bone gap can be measured. Further, at block 704, a therapeutic agent carrier can be selected from a set of therapeutic agent carriers. The therapeutic agent carrier can be selected based on the type of bone having the fracture, the size of the bone, the size of the bone gap, or a combination thereof.

Proceeding to block 706, the selected therapeutic agent carrier can be retrieved from the set of therapeutic agent carriers. At block 708, the therapeutic agent carrier can be cut to size. For example, the therapeutic agent carrier can be sized based on the size of the bone gap measured above.

At block 710, an end of a bone can be accessed. Further, at block 712, a pilot hole can be drilled in the end of the bone. Moving to block 714, a guide wire, or guide pin, can be inserted into a bone canal within the bone through the pilot hole. Thereafter, at block 716, a bone reamer can be inserted into the bone canal over the guide wire.

Proceeding to block 718, the bone canal can be reamed using the bone reamer. At block 720, the bone reamer can be removed from the bone canal. Moving to block 722, an intramedullary rod, or intramedullary nail, can be inserted into the bone canal over the guide wire. At block 724, the guide wire can be removed. Further, at block 726, the therapeutic agent carrier can be wetted with a therapeutic agent. At block 728, the therapeutic agent can be positioned around the intramedullary rod, or intramedullary nail, within the bone gap. Thereafter, at block 730, the therapeutic agent carrier can be sutured in place.

Continuing to block 732, the surgical wound associated with exposing the bone gap can be closed. The surgical wound can be closed by simply allowing the patient's skin to close due to the elasticity of the skin. Alternatively, the surgical wound can be closed using sutures, surgical staples, or any other suitable surgical technique well known in the art. At block 734, post-operative care can be initiated. The method then ends at state 736.

Description of an Alternative Embodiment of a Therapeutic Agent Carrier

Figure 8:
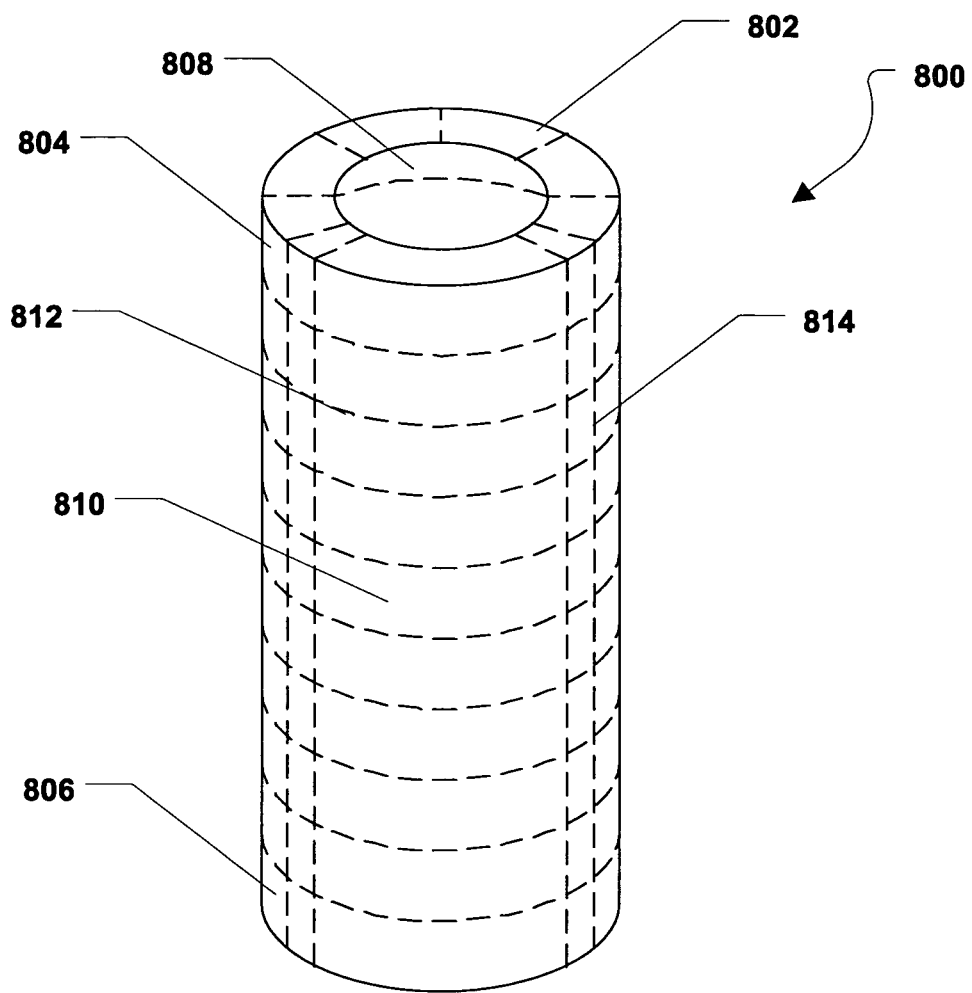
FIG. 8 is a front view of a therapeutic agent carrier.
Figure 9:
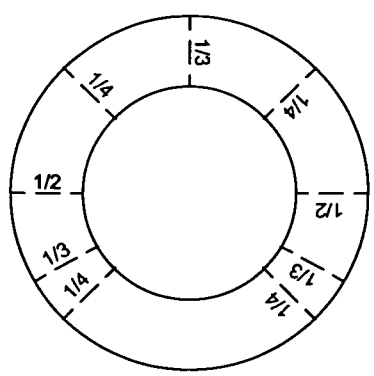
FIG. 9 is an end view of the therapeutic agent carriers.
Figure 10:
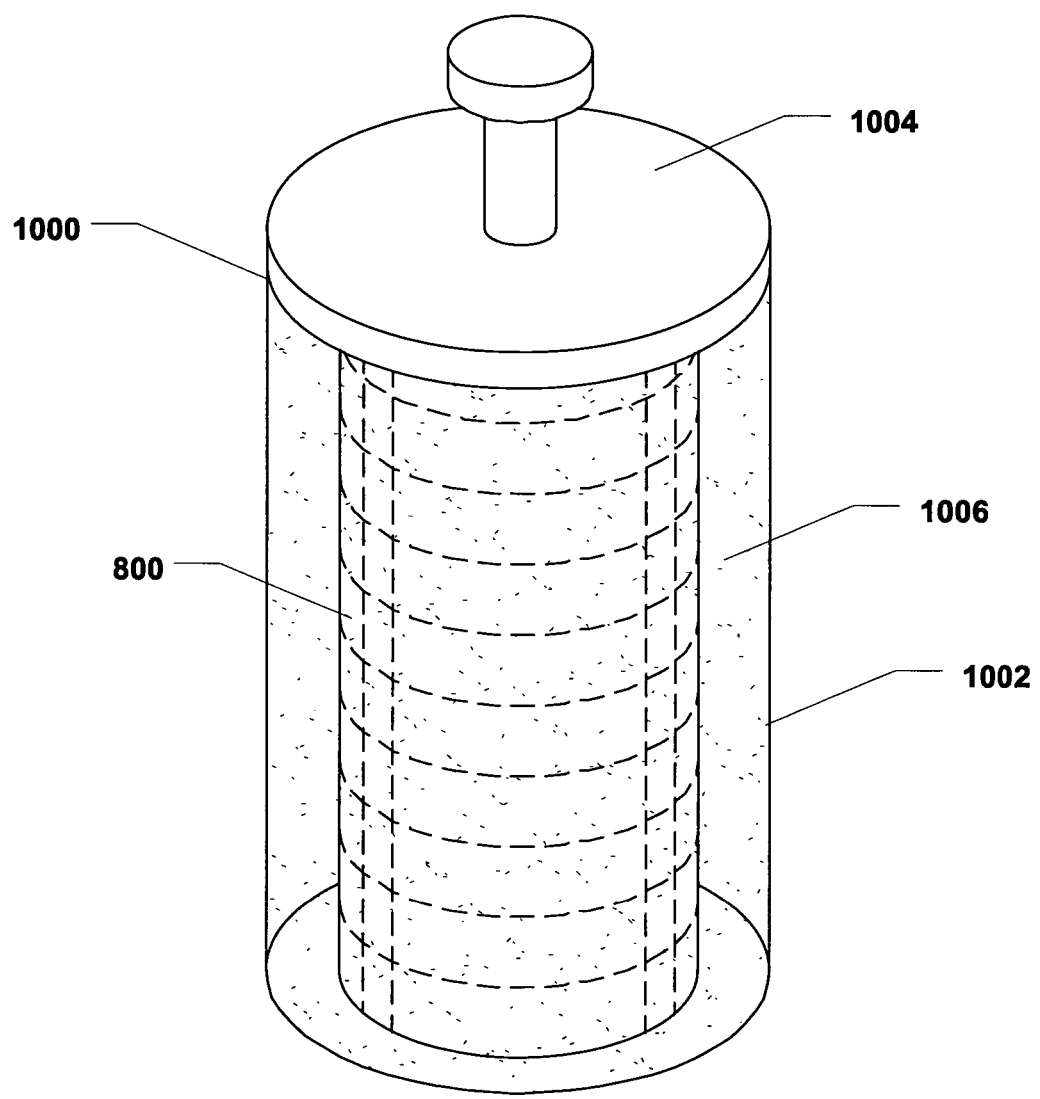
FIG. 10 is another front view of the therapeutic agent carrier.

Referring to FIG. 8 through FIG. 10, an alternative embodiment of a therapeutic agent carrier is shown and is generally designated 800. As shown, the therapeutic agent carrier 800 can include a body 802 that can have a cross-section that is hollow and generally cylindrical. Alternatively, the body 802 of the therapeutic agent carrier 800 can have a cross-section that is generally prismatic shape. Moreover, the body 802 of the therapeutic agent carrier 800 can have any generally polyhedral shape with a central opening formed therein.

In a particular embodiment, the body 802 of the therapeutic agent carrier 800 can include a proximal end 804 and a distal end 806. The body 802 of the therapeutic agent carrier 800 can also include an interior surface 808 and an exterior surface 810.

As illustrated in FIG. 8, the exterior surface 810 of the therapeutic agent carrier 800 can include a plurality of lateral grooves 812 from the proximal end 804 of the body 802 to the distal end 806 of the body 802. In a particular embodiment, the lateral grooves 812 can indicate incremental lengths along the body 802 of the therapeutic agent carrier 800. For example, if the increment is one-half inch, a user may know that by cutting the therapeutic agent carrier 800 along the second incremental groove 812, the therapeutic agent carrier 800 will be approximately one inch long. Further, each lateral groove 812 can serve as a guide for a cutting device, e.g., a saw, a knife, a scalpel, scissors, or other similar device.

FIG. 8 also shows that the body 802 of the therapeutic agent carrier 800 can include a plurality of longitudinal grooves 814 along the length of the body 802. As illustrated in FIG. 9, the longitudinal grooves 814 can be spaced radially around the body 802 of the therapeutic agent carrier 800 and each longitudinal groove 814 can include a label 816. The longitudinal grooves 814 can be labeled so that by cutting similarly labeled longitudinal grooves 814 the therapeutic agent carrier 800 can be cut into halves, thirds, or quarters. For example, two longitudinal grooves 814 can be labeled "½", three longitudinal grooves 814 can be labeled "⅓", and four longitudinal grooves can be labeled "¼". Accordingly, the therapeutic agent carrier 800 shown in FIG. 8 can be cut into pieces that are sized and shaped similarly to the therapeutic agent carriers 202, 204, 206 shown in FIG. 2 through FIG. 4.

Referring to FIG. 10, a container is shown and is designated 1000. As illustrated, the container 1000 includes a base 1002 and a lid 1004. In a particular embodiment, the therapeutic agent carrier 800 can be placed within the container 1000 and the container 1000 can be filled with a therapeutic agent 1006. The therapeutic agent carrier 800 can be porous and as such, the therapeutic agent carrier 800 can be loaded with at least a portion of the therapeutic agent 1006. During surgery, a surgeon, or nurse, can retrieve the therapeutic agent carrier 800 from the container 1000 and cut the therapeutic agent carrier 800 to a size that can be fitted into a bone gap. The therapeutic agent carrier 800 can be pre-loaded due to soaking in the therapeutic agent carrier 800.

In a particular embodiment, any of the therapeutic agent carriers 202, 204, 206 shown in FIG. 2 through FIG. 4 can also be placed within the container 1000 to load in the therapeutic agent 1006. The porosity of the therapeutic agent carriers 202, 204, 206 can be such that a user can determine the dose of material within the therapeutic agent carrier 202, 204, 206 based on the largest dosage stamp 220, 240, 260 on the therapeutic agent carrier 202, 204, 206. For example, if the first therapeutic agent carrier 202 is retrieved from the container 1000 and cut along the fourth groove 218, a user can determine that the dose of the therapeutic agent impregnated within that portion of the first therapeutic agent carrier 202 is eight cubic centimeters (8 cc).

Alternatively, the therapeutic agent carriers 202, 204, 206 can be pre-loaded with a therapeutic agent during manufacturing and the dosage stamps 220, 240, 260 can indicate a dosage available in the pre-loaded therapeutic agent carrier 202, 204, 206. Additionally, the grooves 218, 238, 258 can be lines along which the therapeutic agent carriers 202, 204, 206.

The therapeutic agents can include drugs, cellular matters, biological factors, synthetic osteoinductive peptides, synthetic osteopromotive peptides, or a combination thereof. In a particular embodiment, the drugs can include antibiotics, analgesics, anti-inflammatory drugs, anti-TNF-alpha, steroids, or a combination thereof. Further, the cellular matters can include bone marrow derived stem cells, lipo derived stem cells, or a combination thereof. Also, the biological factor can include bone morphogenetic protein (BMP), cartilage-derived morphogenetic protein (CDMP), platelet derived growth factor (PDGF), insulin-like growth factor (IGF), LIM mineralization protein, fibroblast growth factor (FGF), osteoblast growth factor, growth and differentiation factor (GDF), vascular endothelial growth factor (VEGF), or a combination thereof. The synthetic osteoinductive peptide or the synthetic osteopromotive peptide can include a fragment of a thrombin molecule. Also, the GDF can include GDF-5.

Description of a Set of Bone Cutting Templates

Figure 11:
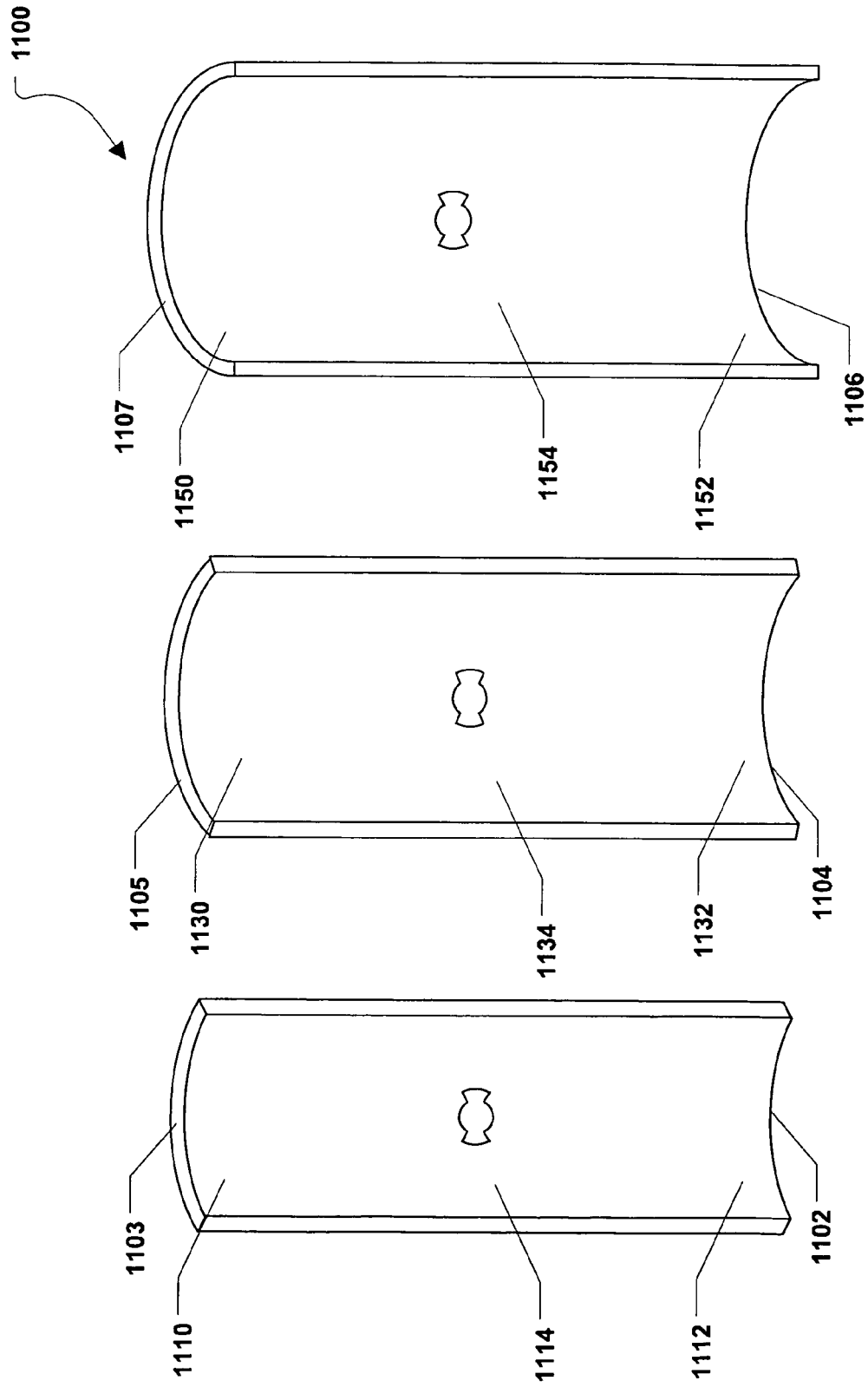
FIG. 11 is a front view of a set of bone cutting templates.
Figure 12:
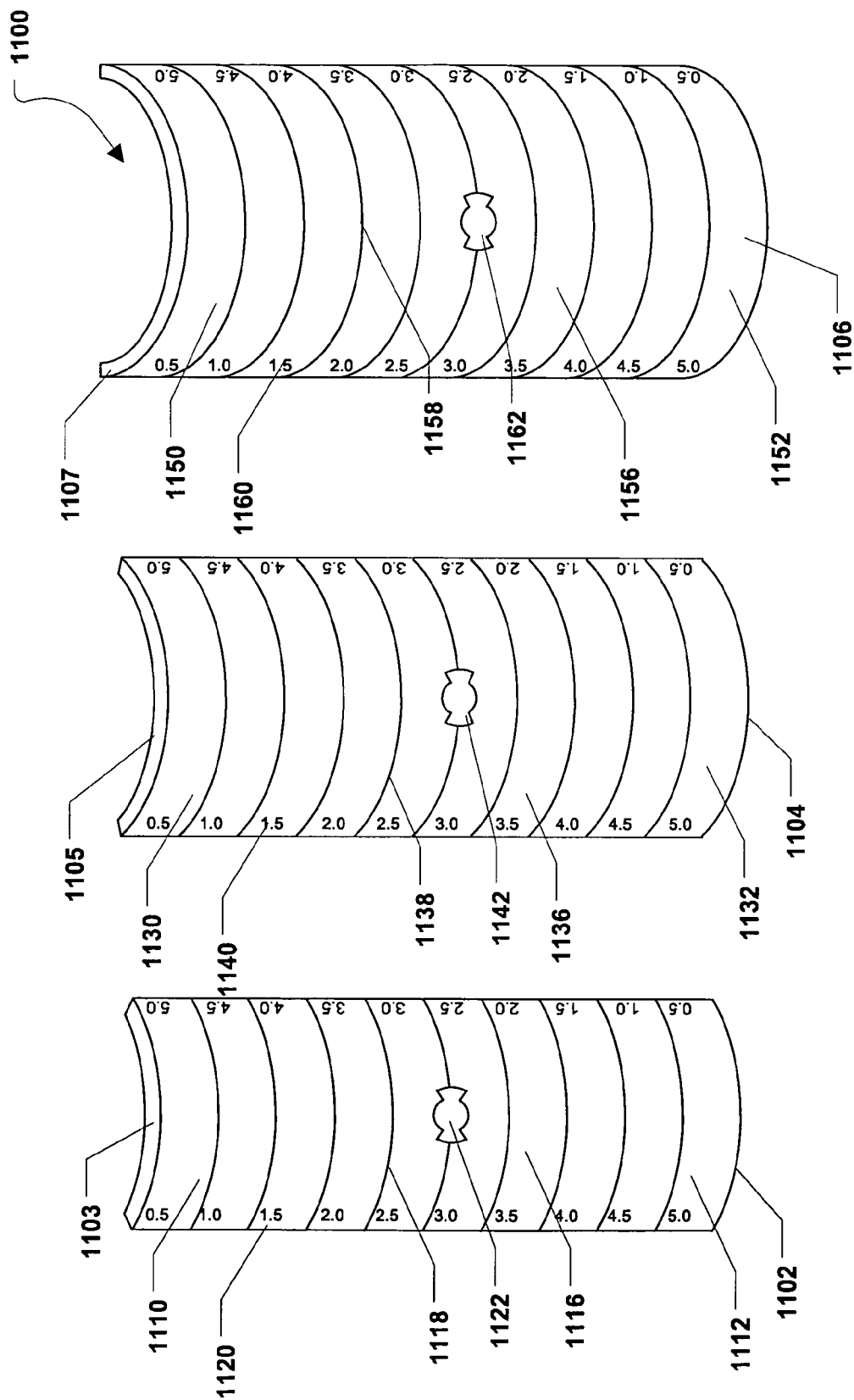
FIG. 12 is a rear view of the set of bone cutting templates.
Figure 13:
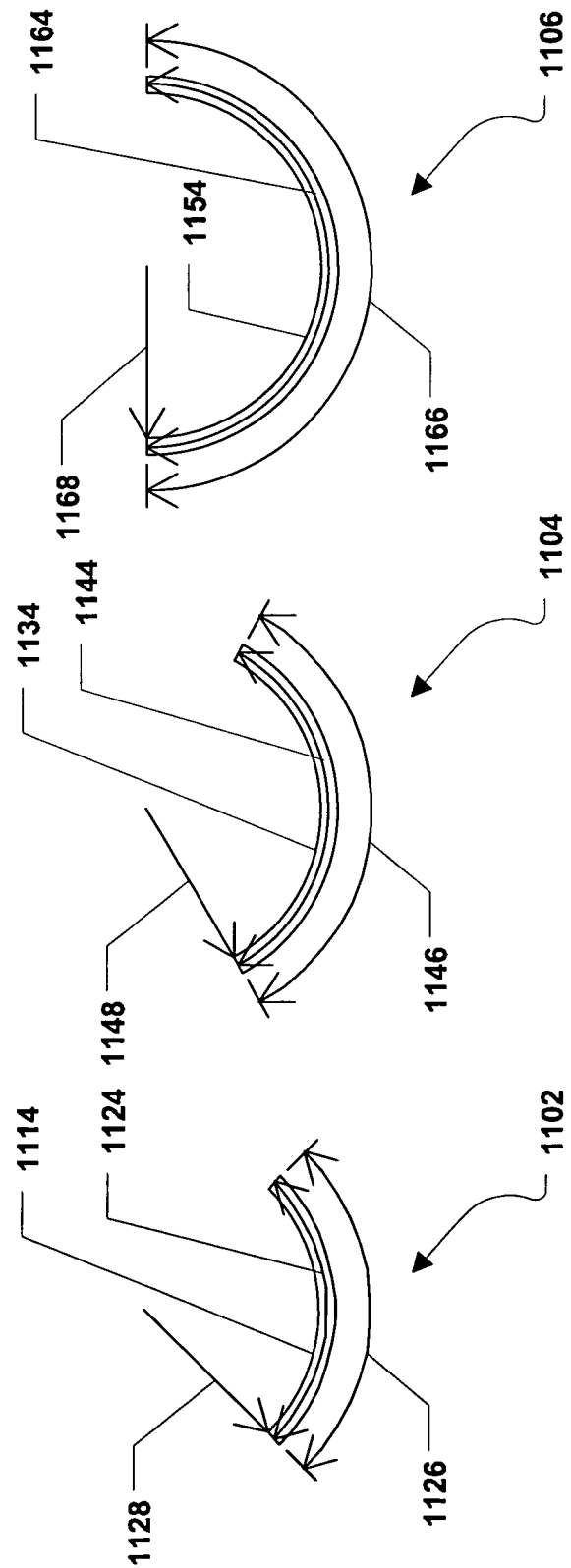
FIG. 13 is an end view of the set of bone cutting templates.

Referring to FIG. 11 through FIG. 13, a set of bone cutting templates is shown and is generally designated 1100. As shown, the set of bone cutting templates 1100 can include a first bone cutting template 1102, a second bone cutting template 1104, and a third bone cutting template 1106.

In a particular embodiment, the first bone cutting template 1102 can include a body 1103 having a proximal end 1110 and a distal end 1112. The body 1103 of first bone cutting template 1102 can also include an interior surface 1114 and an exterior surface 1116. In a particular embodiment, the body 1103 of the first bone cutting template 1102 can be made from one or more biocompatible materials. For example, the materials can be metal containing materials, polymer materials, or composite materials that include metals, polymers, or combinations of metals and polymers.

In a particular embodiment, the metal containing materials can be metals. Further, the metal containing materials can be ceramics. Also, the metals can be pure metals or metal alloys. The pure metals can include titanium. Moreover, the metal alloys can include stainless steel, a cobalt-chrome-molybdenum alloy, e.g., ASTM F-999 or ASTM F-75, a titanium alloy, or a combination thereof.

The polymer materials can include polyurethane materials, polyolefin materials, polyaryletherketone (PAEK) materials, or a combination thereof. Further, the polyolefin materials can include polypropylene, polyethylene, halogenated polyolefin, flouropolyolefin, or a combination thereof. The polyaryletherketon (PAEK) materials can include polyetherketone (PEK), polyetheretherketone (PEEK), polyetherketoneketone (PEKK), polyetherketoneetherketoneketone (PEKEKK), or a combination thereof. Alternatively, the body 1103 can be made from any other substantially rigid biocompatible materials.

As illustrated in FIG. 12, the exterior surface 1116 of the first bone cutting template 1102 can include a plurality of incremental grooves 1118 from the proximal end 1110 of the first bone cutting template 1102 to the distal end 1112 of the bone cutting template 1102. In a particular embodiment, the incremental grooves 1118 can indicate incremental lengths along the first bone cutting template 1102.

FIG. 12 further indicates that the bone cutting template 1102 can include a length stamp 1120 adjacent to each incremental groove 1118. In a particular embodiment, each length stamp 1120 can indicate a length along the bone cutting template 1102.

In a particular embodiment, the first bone cutting template 1102 can be stamped bi-directionally. In other words, the first bone cutting template 1102 can be marked with a first incremental series of length stamps 1120 that can be read from a first side of the first bone cutting template 1102 (i.e., length stamps can be oriented in an upright position relative to the first side of the template). Also, the first bone cutting template 1102 can be marked with a second incremental series of length stamps 1120 that can be read from a second side of the first bone cutting template 1102 (i.e., length stamps can be oriented in an upright position relative to the second side of the template).

During surgery, the first bone cutting template 1102 can be placed over a bone defect, or bone void. Further, a surgeon can use the first bone cutting template 1102 as a guide to trim the perimeter of the bone defect to allow a therapeutic agent carrier, e.g., a therapeutic agent carrier according to one or more of the embodiments described herein, to be fitted into the opening created. The surgeon can trim one edge of the bone defect using the first bone cutting template 1102 and then, the surgeon may slide the first bone cutting template 1102 relative to the bone defect and align one of the incremental grooves 1118 with the trimmed edge in order to create an opening that is shorter than the overall length of the first bone cutting template 1102. Further, the surgeon can measure the size of the opening created using the length stamps 1120 along the first bone cutting template 1102. The length stamps 1120 can be used to measure a bone gap before or after the bone around the bone gap is cut around the template.

FIG. 12 further indicates that the first bone cutting template 1102 can include a central opening 1122 therethrough. In a particular embodiment, the central opening 1122 is keyed to a tip of a bone cutting template handle, described below. In other words, the central opening 1122 of the first bone cutting template 1102 is sized and shaped to receive the tip of the bone cutting template handle and removably engage the tip of the bone cutting template handle.

Referring now to FIG. 13, the first bone cutting template 1102 has a cross-section that can follow an arc 1124 having a central angle 1126 that is substantially equal to ninety degrees (90°). As such, the first bone cutting template 1102 has a cross-section that is equal to one-quarter of a hollow cylinder. Further, the interior surface 1114 of the first bone cutting template 1102 can define a radius 1128. In a particular embodiment, the radius 1128 of the exterior surface 1116 can be configured to approximate the outer cortex of a bone to be treated. For example, the radius 1128 of the interior surface 1114 can be in a range from one centimeter (1 cm) to six centimeters (6 cm). Further, for treating radii bones, the radius 1128 can be in a range from two centimeters (2 cm) to three and one-half centimeters (3.5 cm). Also, for treating femurs, the radius 1128 can be in a range from two centimeters (2 cm) to four centimeters (4 cm).

In a particular embodiment, the second bone cutting template 1104 can include a body 1105 having a proximal end 1130 and a distal end 1132. The body 1105 of second bone cutting template 1104 can also include an interior surface 1134 and an exterior surface 1136. In a particular embodiment, the body 1105 of the second bone cutting template 1104 can be made from one or more biocompatible materials. For example, the materials can be metal containing materials, polymer materials, or composite materials that include metals, polymers, or combinations of metals and polymers.

In a particular embodiment, the metal containing materials can be metals. Further, the metal containing materials can be ceramics. Also, the metals can be pure metals or metal alloys. The pure metals can include titanium. Moreover, the metal alloys can include stainless steel, a cobalt-chrome-molybdenum alloy, e.g., ASTM F-999 or ASTM F-75, a titanium alloy, or a combination thereof.

The polymer materials can include polyurethane materials, polyolefin materials, polyaryletherketone (PAEK) materials, or a combination thereof. Further, the polyolefin materials can include polypropylene, polyethylene, halogenated polyolefin, flouropolyolefin, or a combination thereof. The polyaryletherketon (PAEK) materials can include polyetherketone (PEK), polyetheretherketone (PEEK), polyetherketoneketone (PEKK), polyetherketoneetherketoneketone (PEKEKK), or a combination thereof. Alternatively, the body 1105 can be made from any other substantially rigid biocompatible materials.

As illustrated in FIG. 12, the exterior surface 1136 of the second bone cutting template 1104 can include a plurality of incremental grooves 1138 from the proximal end 1130 of the second bone cutting template 1104 to the distal end 1132 of the bone cutting template 1104. In a particular embodiment, the incremental grooves 1138 can indicate incremental lengths along the second bone cutting template 1104.

FIG. 12 further indicates that the second bone cutting template 1104 can include a length stamp 1140 adjacent to each incremental groove 1138. In a particular embodiment, each length stamp 1140 can indicate a length along the bone cutting template 1104.

In a particular embodiment, the second bone cutting template 1104 can be stamped bi-directionally. In other words, the second bone cutting template 1104 can be marked with a first incremental series of length stamps 1140 that can be read from a first side of the second bone cutting template 1104. Also, the second bone cutting template 1104 can be marked with a second incremental series of length stamps 1140 that can be read from a second side of the second bone cutting template 1104.

During surgery, the second bone cutting template 1104 can be place over a bone defect, or bone void. Further, a surgeon can use the second bone cutting template 1104 as a guide to trim the perimeter of the bone defect to allow a therapeutic agent carrier, e.g., a therapeutic agent carrier according to one or more of the embodiments described herein, to be fitted into the opening created. The surgeon can trim one edge of the bone defect using the second bone cutting template 1104 and then, the surgeon may slide the second bone cutting template 1104 relative to the bone defect and align one of the incremental grooves 1138 with the trimmed edge in order to create an opening that is shorter than the overall length of the second bone cutting template 1104. Further, the surgeon can measure the size of the opening created using the length stamps 1140 along the second bone cutting template 1104. The length stamps 1140 can be used to measure a bone gap before or after the bone around the bone gap is cut around the template.

FIG. 12 further indicates that the second bone cutting template 1104 can include a central opening 1142 therethrough. In a particular embodiment, the central opening 1142 is keyed to a tip of a bone cutting template handle, described below. In other words, the central opening 1142 of the second bone cutting template 1104 is sized and shaped to receive the tip of the bone cutting template handle and removably engage the tip of the bone cutting template handle.

Referring to FIG. 13, the second bone cutting template 1104 has a cross-section that can follow an arc 1144 having a central angle 1146 that is substantially equal to one hundred and twenty degrees (120°). As such, the second bone cutting template 1104 has a cross-section that is equal to one-third of a hollow cylinder. Further, the interior surface 1134 of the second bone cutting template 1104 can define a radius 1148. In a particular embodiment, the radius 1148 of the interior surface 1134 can be configured to approximate the outer cortex of a bone to be treated. For example, the radius 1148 of the interior surface 1134 can be in a range from one centimeter (1 cm) to six centimeters (6 cm). Further, for treating radii bones, the radius 1148 can be in a range from two centimeters (2 cm) to three and one-half centimeters (3.5 cm). Also, for treating femurs, the radius 1148 can be in a range from two centimeters (2 cm) to four centimeters (4 cm).

In a particular embodiment, the third bone cutting template 1106 can include a body 1107 having a proximal end 1150 and a distal end 1152. The body 1107 of third bone cutting template 1106 can also include an interior surface 1154 and an exterior surface 1156. In a particular embodiment, the body 1107 of the third bone cutting template 1106 can be made from one or more biocompatible materials. For example, the materials can be metal containing materials, polymer materials, or composite materials that include metals, polymers, or combinations of metals and polymers.

In a particular embodiment, the metal containing materials can be metals. Further, the metal containing materials can be ceramics. Also, the metals can be pure metals or metal alloys. The pure metals can include titanium. Moreover, the metal alloys can include stainless steel, a cobalt-chrome-molybdenum alloy, e.g., ASTM F-999 or ASTM F-75, a titanium alloy, or a combination thereof.

The polymer materials can include polyurethane materials, polyolefin materials, polyaryletherketone (PAEK) materials, or a combination thereof. Further, the polyolefin materials can include polypropylene, polyethylene, halogenated polyolefin, flouropolyolefin, or a combination thereof. The polyaryletherketon (PAEK) materials can include polyetherketone (PEK), polyetheretherketone (PEEK), polyetherketoneketone (PEKK), polyetherketoneetherketoneketone (PEKEKK), or a combination thereof. Alternatively, the body 1107 can be made from any other substantially rigid biocompatible materials.

As illustrated in FIG. 12, the exterior surface 1156 of the third bone cutting template 1106 can include a plurality of incremental grooves 1158 from the proximal end 1150 of the third bone cutting template 1106 to the distal end 1152 of the bone cutting template 1106. In a particular embodiment, the incremental grooves 1158 can indicate incremental lengths along the third bone cutting template 1106.

FIG. 12 further indicates that the bone cutting template 1106 can include a length stamp 1160 adjacent to each incremental groove 1158. In a particular embodiment, each length stamp 1160 can indicate a length along the bone cutting template 1106.

In a particular embodiment, the third bone cutting template 1106 can be stamped bi-directionally. In other words, the third bone cutting template 1106 can be marked with a first incremental series of length stamps 1160 that can be read from a first side of the third bone cutting template 1106. Also, the third bone cutting template 1106 can be marked with a second incremental series of length stamps 1160 that can be read from a second side of the third bone cutting template 1106.

During surgery, the third bone cutting template 1106 can be place over a bone defect, or bone void. Further, a surgeon can use the third bone cutting template 1106 as a guide to trim the perimeter of the bone defect to allow a therapeutic agent carrier, e.g., a therapeutic agent carrier according to one or more of the embodiments described herein, to be fitted into the opening created. The surgeon can trim one edge of the bone defect using the third bone cutting template 1106 and then, the surgeon may slide the third bone cutting template 1106 relative to the bone defect and align one of the incremental grooves 1158 with the trimmed edge in order to create an opening that is shorter than the overall length of the third bone cutting template 1106. Further, the surgeon can measure the size of the opening created using the length stamps 1160 along the third bone cutting template 1106. The length stamps 1160 can be used to measure a bone gap before or after the bone around the bone gap is cut around the template.

FIG. 12 further indicates that the third bone cutting template 1106 can include a central opening 1162 therethrough. In a particular embodiment, the central opening 1162 is keyed to a tip of a bone cutting template handle, described below. In other words, the central opening 1162 of the third bone cutting template 1106 is sized and shaped to receive the tip of the bone cutting template handle and removably engage the tip of the bone cutting template handle.

Still referring to FIG. 13, the third bone cutting template 1106 has a cross-section that can follow an arc 1164 having a central angle 1166 that is substantially equal to one hundred and eighty degrees (180°). As such, the third bone cutting template 1106 has a cross-section that is equal to one-half of a hollow cylinder, i.e., the third bone cutting template 1106 has a cross-section that is equal to a hollow semi-cylinder. Further, the interior surface 1154 of the third bone cutting template 1106 can define a radius 1168. In a particular embodiment, the radius 1168 of the interior surface 1154 can be configured to approximate the outer cortex of a bone to be treated. For example, the radius 1168 of the interior surface 1154 can be in a range from one centimeter (1 cm) to six centimeters (6 cm). Further, for treating radii bones, the radius 1168 can be in a range from two centimeters (2 cm) to three and one-half centimeters (3.5 cm). Also, for treating femurs, the radius 1168 can be in a range from two centimeters (2 cm) to four centimeters (4 cm).

Description of a Bone Cutting Template Handle

Figure 14:
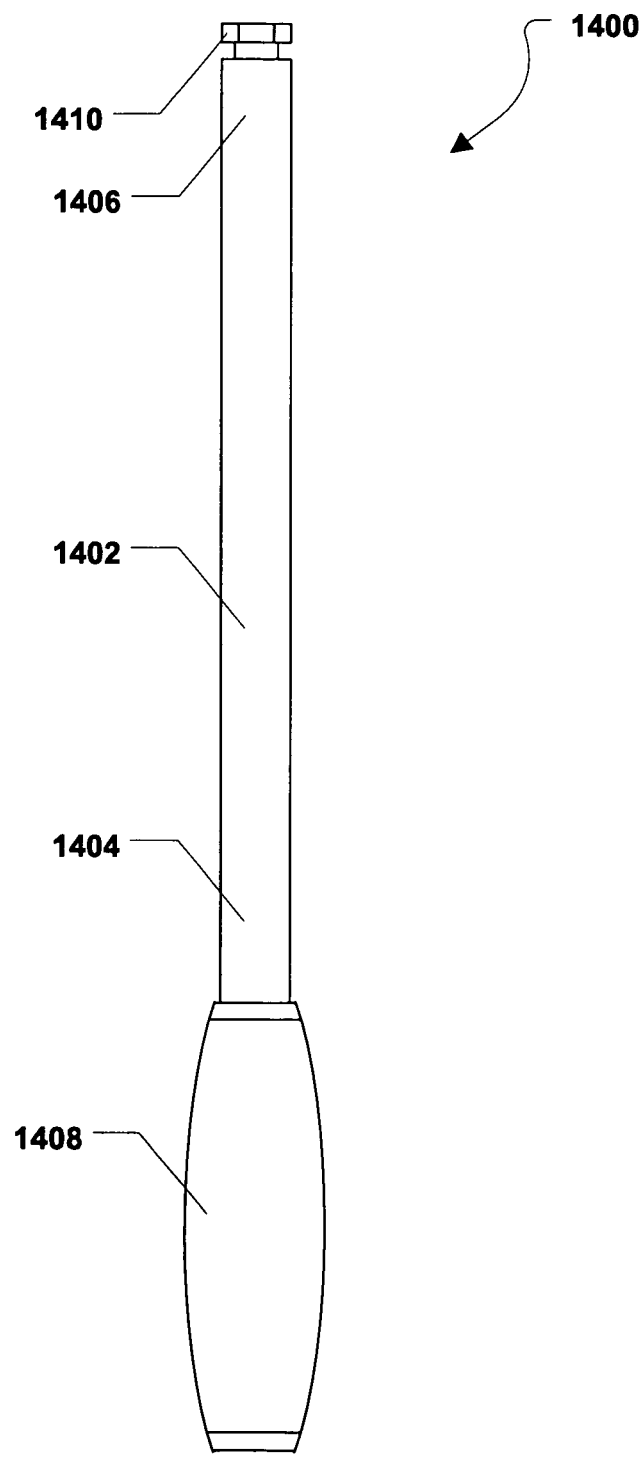
FIG. 14 is a plan view of a bone cutting template handle.
Figure 15:
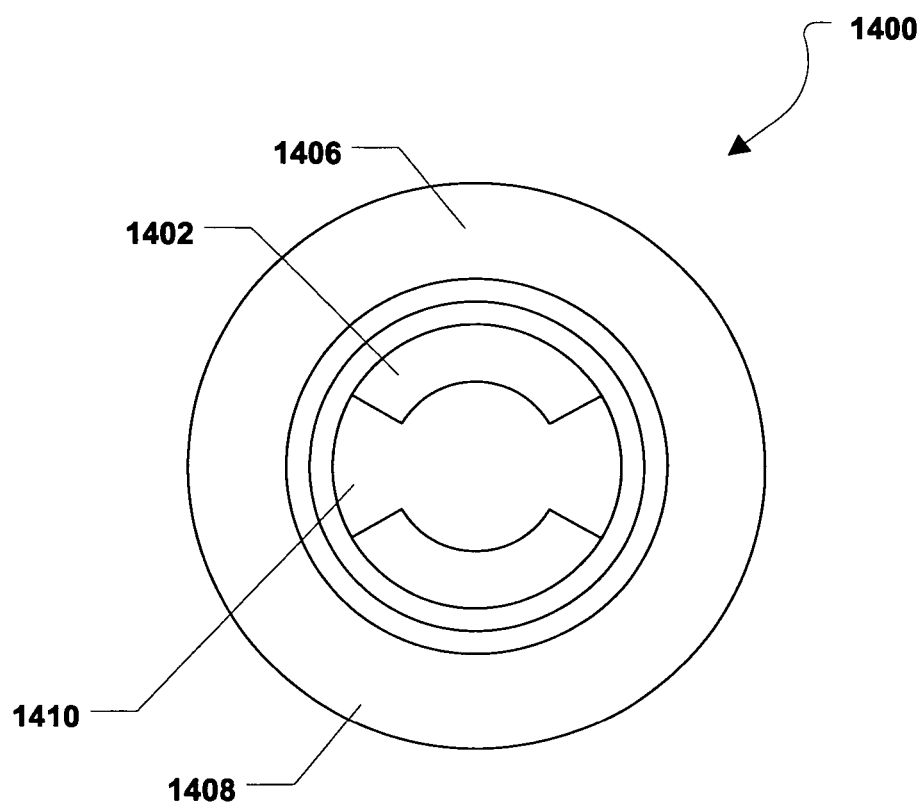
FIG. 15 is an end view of the bone cutting template handle.

Referring to FIG. 14 and FIG. 15, a bone cutting template handle is shown and is generally designated 1400. As shown, the bone cutting template handle 1400 can include a body 1402 that can include a proximal end 1404 and a distal end 1406. A handle 1408 can be attached to the proximal end 1404 of the body 1402.

Figure 16:
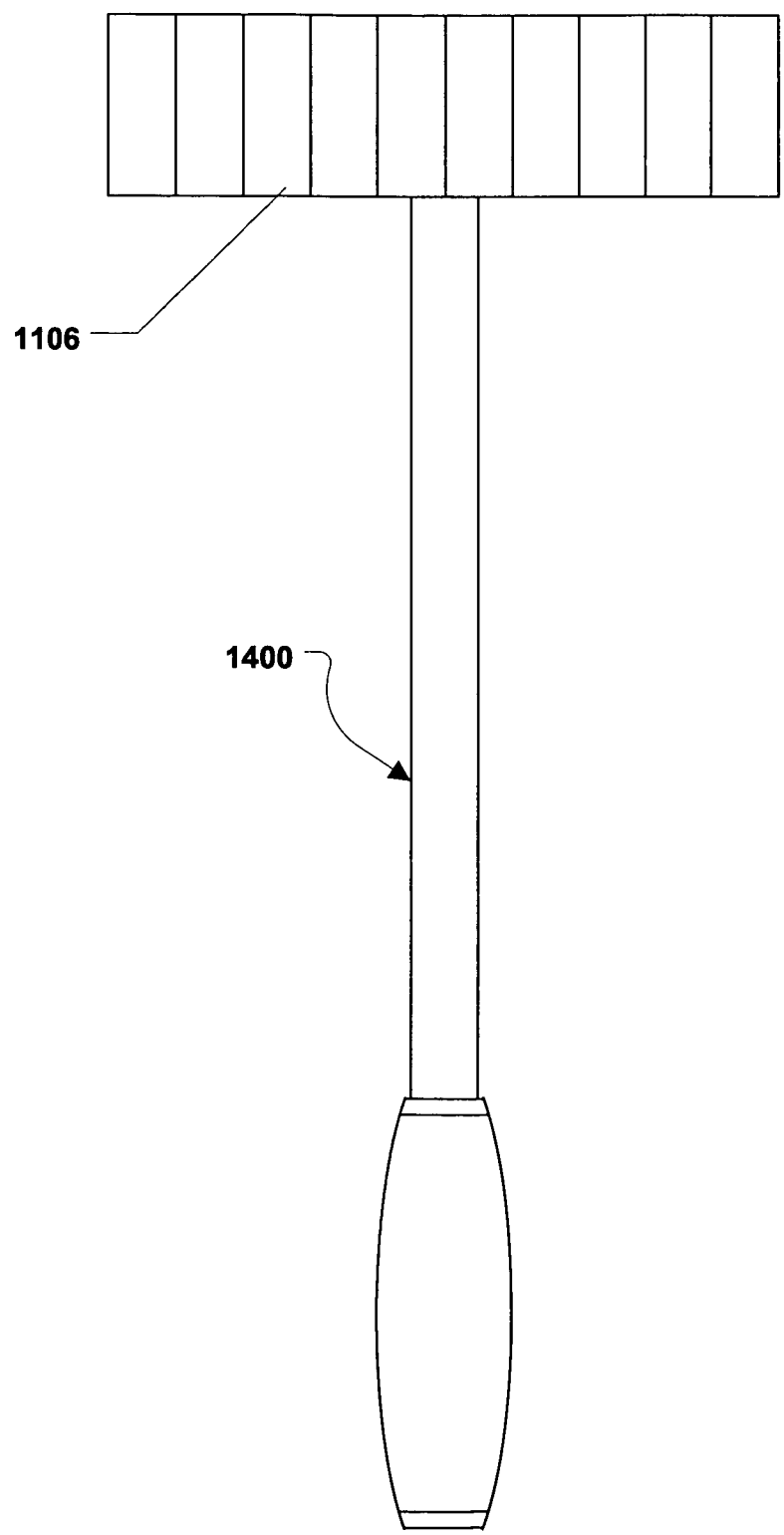
FIG. 16 is a plan view of a bone cutting template engaged with a bone cutting template handle.

Further, as shown in FIG. 15, the distal end 1406 of the body 1402 can include a tip 1410 that is keyed to the bone cutting templates 1102, 1104, 1106. In other words, the tip 1410 of the bone cutting template handle 1400 is sized and shaped to be inserted into the central opening 1122, 1142, 1162 of each bone cutting template 1102, 1104, 1106. As such, the tip 1410 of the bone cutting template handle 1400 can be inserted into a central opening 1122, 1142, 1162 of a bone cutting template 1102, 1104, 1106 and the bone cutting template handle 1400 can be rotated to lock the tip 1410 of the bone cutting template handle 1400 within a bone cutting template, e.g., the third bone cutting template 1106, as shown in FIG. 16.

During surgery, a surgeon can select an appropriate bone cutting template 1102, 1104, 1106 from a set of bone cutting templates 1100 and use the bone cutting template 1102, 1104, 1106 to trim a bone gap so that a therapeutic agent carrier, e.g., a therapeutic agent carrier according to one or more of the embodiments described herein, can fit within the bone gap.

Description of a Third Method of Treating a Bone Fracture

Figure 17:
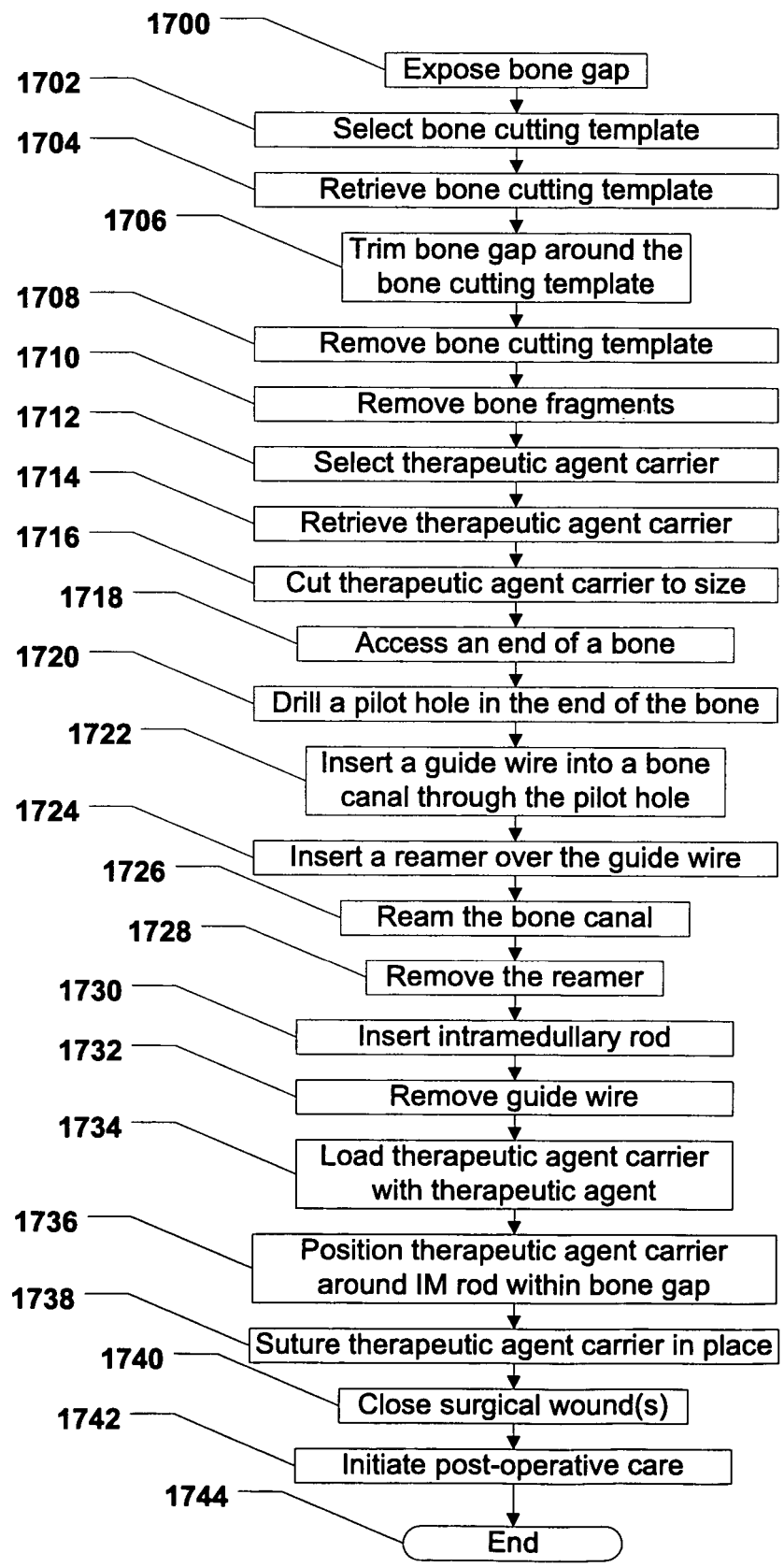
FIG. 17 is a flow chart of a third method of treating a bone fracture.

Referring to FIG. 17, a third method of treating a bone fracture is shown and commences at block 1700. At block 1700, a bone gap due to a fracture in the bone can be exposed. At block 1702, a bone cutting template can be selected. Thereafter, at block 1704, the selected bone cutting template can be retrieved. In a particular embodiment, the selected bone cutting template can be retrieved by engaging a bone cutting template handle with the selected bone cutting template. At block 1706, the bone gap can be trimmed around the bone cutting template. In a particular embodiment, the bone gap can be trimmed using a medical saw. At block 1708, the bone cutting template can be removed from the surgical field. Also, at block 1710, any bone fragments can be removed from the surgical field.

Moving to block 1712, a therapeutic agent carrier can be selected from a set of therapeutic agent carriers. The therapeutic agent carrier can be selected based on the type of bone having the fracture, the size of the bone, the size of the bone gap, or a combination thereof. At block 1714, the selected therapeutic agent carrier can be retrieved from the set of therapeutic agent carriers. Further, at block 1716, the therapeutic agent carrier can be cut to size. For example, the therapeutic agent carrier can be sized based on the size of the bone gap measured above.

At block 1718, an end of a bone can be accessed. Further, at block 1720, a pilot hole can be drilled in the end of the bone. Moving to block 1722, a guide wire, or guide pin, can be inserted into a bone canal within the bone through the pilot hole. Thereafter, at block 1724, a bone reamer can be inserted into the bone canal over the guide wire.

Proceeding to block 1726, the bone canal can be reamed using the bone reamer. At block 1728, the bone reamer can be removed from the bone canal. Moving to block 1730, an intramedullary rod, or intramedullary nail, can be inserted into the bone canal over the guide wire. At block 1732, the guide wire can be removed. Further, at block 1734, the therapeutic agent carrier can be wetted with a therapeutic agent. At block 1736, the therapeutic agent can be positioned around the intramedullary rod, or intramedullary nail, within the bone gap. Thereafter, at block 1738, the therapeutic agent carrier can be sutured in place.

Continuing to block 1740, the surgical wound associated with exposing the bone gap can be closed. The surgical wound can be closed by simply allowing the patient's skin to close due to the elasticity of the skin. Alternatively, the surgical wound can be closed using sutures, surgical staples, or any other suitable surgical technique well known in the art. At block 1742, post-operative care can be initiated. The method then ends at state 1744.

Conclusion

With the configuration of structure described above, the therapeutic agent carrier provides a device that can be used to deliver a therapeutic agent to an area within a bone defect. A therapeutic agent carrier can be selected from a group of therapeutic agent carriers and cut to size to fit within the bone defect. Further, prior to positioning within the bone defect, the therapeutic agent carrier can be loaded with a therapeutic agent. Also, the bone cutting templates provide a device that can be used to trim a bone defect prior to installing the therapeutic agent carrier.

The above-disclosed subject matter is to be considered illustrative, and not restrictive, and the appended claims are intended to cover all such modifications, enhancements, and other embodiments that fall within the true spirit and scope of the present invention. Thus, to the maximum extent allowed by law, the scope of the present invention is to be determined by the broadest permissible interpretation of the following claims and their equivalents, and shall not be restricted or limited by the foregoing detailed description.

What is claimed is:

1. A bone cutting template, comprising:
   a body having an axis, an axial length and an axial cross-sectional shape that is semi-cylindrical along the axial length with a concave inner surface and a convex outer surface, wherein the semi-cylindrical body is formed at a radius in a range of one to six centimeters, and the body terminates at circumferential ends of the body;
   a plurality of grooves formed on the convex outer surface of the body along the axial length, wherein each groove corresponds to an incremental axial length of the body, and the grooves extend from one circumferential end of the body to the other;
   a plurality of length stamps along the convex outer surface of the body, wherein each of the plurality of length stamps is adjacent to a corresponding groove and indicates a length along the bone cutting template;
   a proximal end; and
   a distal end,
   wherein the plurality of length stamps comprises a first set of length stamps and a second set of length stamps, the first set of length stamps increase in value from the proximal end to the distal end, and the first set of length stamps has a first orientation relative to a first side of the bone cutting template, the second set of length stamps increase in value from the distal end to the proximal end, the second set of length stamps has a second orientation relative to a second side of the bone cutting template, and the second orientation is opposite to the first orientation.

2. The bone cutting template of claim 1, wherein the concave inner surface is semi-cylindrical in shape to approximate an outer cortex of a bone, and the body has a radial thickness in a range of one to six centimeters.

3. The bone cutting template of claim 1, wherein the semi-cylindrical shape of the body forms an arch having an angular displacement of one hundred and eighty degrees, and the body is substantially rigid.

4. The bone cutting template of claim 1, wherein the semi-cylindrical shape of the body forms an arch having an angular displacement of one hundred and twenty degrees and the body is formed from a material selected from the group consisting of ceramic, collagen-ceramic, a degradable polymer, and a combination thereof.

5. The bone cutting template of claim 1, wherein the semi-cylindrical shape of the body forms an arch having an angular displacement of ninety degrees.

6. The bone cutting template of claim 1, further comprising:
   a central opening formed in the body at an axial center of the body; and
   a bone cutting template handle configured to removably engage the central opening.

7. The bone cutting template of claim 6, wherein the bone cutting template handle comprises a grip on a proximal end thereof, a shaft extending from the grip, and a tip at a distal end of the shaft that is keyed to and complementary in shape to the central opening for removable engagement therewith.

8. The bone cutting template of claim 1, wherein the body is porous and further comprises a therapeutic agent.

9. A kit for field use, comprising:
   a set of bone cutting templates, wherein each of the bone cutting templates comprises:
      a body having an axis; an axial length; an axial cross-sectional shape that is semi-cylindrical along the axial length with a concave inner surface and a convex outer surface; a proximal end; and a distal end, wherein each of the semi-cylindrical bodies is formed at a radius in a range of one to six centimeters, and the bodies terminate at circumferential ends of the bodies;
      a plurality of grooves formed on the convex outer surface of the body along the axial length, wherein each groove corresponds to an incremental axial length of the body, and the grooves extend from one circumferential end of the body to the other: and
      a plurality of length stamps along the convex outer surface of the body, wherein each of the plurality of length stamps is adjacent to a corresponding groove and indicates a length along the bone cutting template, wherein the plurality of length stamps comprises a first set of length stamps and a second set of length stamps, the first set of length stamps increase in value from the proximal end to the distal end, and the first set of length stamps has a first orientation relative to a first side of the bone cutting template, the second set of length stamps increase in value from the distal end to the proximal end, the second set of length stamps has a second orientation relative to a second side of the bone cutting template, and the second orientation is opposite to the first orientation; and
   a bone cutting template handle configured to removably engage each of the bone cutting templates.

10. The kit of claim 9, wherein the concave inner surface of each of the bodies is semi-cylindrical in shape to approximate an outer cortex of a bone, and each of the bodies has a radial thickness in a range of one to six centimeters.

11. The kit of claim 9, wherein each of the semi-cylindrical shapes of the bodies forms an arch having an angular displacement that differs from other ones of the bodies, and the bodies are substantially rigid.

12. The kit of claim 11, wherein the angular displacement of each of the semi-cylindrical shapes of the bodies comprises one of one hundred and eighty degrees, one hundred and twenty degrees, and ninety degrees, and the bodies are formed form a material selected from the group consisting of ceramic, collagen-ceramic, a degradable polymer, and a combination thereof.

13. The kit of claim 9, wherein each of the bodies further comprises:
   a central opening formed in the body at an axial center of the body for removable engagement by the bone cutting template handle.

14. The kit of claim 13, wherein the bone cutting template handle comprises a grip on a proximal end thereof, a shaft extending from the grip, and a tip at a distal end of the shaft that is keyed and complementary in shape to the central opening for removable engagement therewith.

15. The kit of claim 9, wherein the body is porous and further comprises a therapeutic agent.

\* \* \* \* \*

UNITED STATES PATENT AND TRADEMARK OFFICE
CERTIFICATE OF CORRECTION

PATENT NO. : 8,469,964 B2  
APPLICATION NO. : 11/431693  
DATED : June 25, 2013  
INVENTOR(S) : Scifert et al.

Page 1 of 1

It is certified that error appears in the above-identified patent and that said Letters Patent is hereby corrected as shown below:

In the Specification

In Column 5, Line 49, delete "FIG. 3,." and insert -- FIG. 3, --, therefor.

In Column 10, Lines 20-21, delete "polyaryletherketon" and insert -- polyaryletherketone --, therefor.

In Column 11, Lines 46-47, delete "polyaryletherketon" and insert -- polyaryletherketone --, therefor.

In Column 13, Lines 2-3, delete "polyaryletherketon" and insert -- polyaryletherketone --, therefor.

In the Claims

In Column 16, Line 46, in Claim 9, delete "other:" and insert -- other; --, therefor.

In Column 17, Lines 8-9, in Claim 12, delete "formed form" and insert -- formed from --, therefor.

In Column 17, Line 20, in Claim 14, delete "keyed and" and insert -- keyed to and --, therefor.

Signed and Sealed this  
Twenty-second Day of October, 2013

Teresa Stanek Rea  
*Deputy Director of the United States Patent and Trademark Office*